US012023035B2

(12) United States Patent
Dasnurkar et al.

(10) Patent No.: US 12,023,035 B2
(45) Date of Patent: Jul. 2, 2024

(54) ADHESIVE OCCLUSION SYSTEMS

(71) Applicant: Terumo Corporation, Tokyo (JP)

(72) Inventors: Anup Dasnurkar, Tokyo (JP); Shawn O'Leary, Tokyo (JP); Maricela D. Walker, Tokyo (JP); Brian Gray, Tokyo (JP); Michael Martel, Tokyo (JP)

(73) Assignee: Terumo Corporation, Tokyo (JP)

( * ) Notice: Subject to any disclaimer, the term of this patent is extended or adjusted under 35 U.S.C. 154(b) by 338 days.

(21) Appl. No.: 17/169,177

(22) Filed: Feb. 5, 2021

(65) Prior Publication Data

US 2021/0153870 A1 May 27, 2021

Related U.S. Application Data

(63) Continuation of application No. 15/990,458, filed on May 25, 2018, now Pat. No. 10,952,740.

(Continued)

(51) Int. Cl.
*A61B 17/12* (2006.01)
*A61B 17/00* (2006.01)
(Continued)

(52) U.S. Cl.
CPC .. *A61B 17/12122* (2013.01); *A61B 17/12031* (2013.01); *A61B 17/12136* (2013.01); *A61B 17/1214* (2013.01); *A61B 17/12168* (2013.01); *A61B 17/12172* (2013.01); *A61B 17/12186* (2013.01); *A61B 17/12195* (2013.01); *A61B 2017/005* (2013.01);
(Continued)

(58) Field of Classification Search
CPC .............. A61B 17/12; A61B 17/12122; A61B 17/1214; A61B 17/12031; A61B 17/12136; A61B 17/12168; A61B 17/12172; A61B 17/12186; A61B 17/12195; A61B 2017/005; A61F 2/95; A61F 2/958
See application file for complete search history.

(56) References Cited

U.S. PATENT DOCUMENTS 4,364,392 A  12/1982 Strother et al.
5,067,489 A  11/1991 Lind
(Continued)

FOREIGN PATENT DOCUMENTS

CN  102438533 A  5/2012
EP  1691879 B1  8/2006
(Continued)

OTHER PUBLICATIONS

Japanese Patent Office, Office Action dated Jul. 6, 2022 with English translation in Japanese Patent Application No. 2019-565293, 12 pages.
(Continued)

*Primary Examiner* — Vi X Nguyen
(74) *Attorney, Agent, or Firm* — Inskeep IP Group, Inc.

(57) ABSTRACT

System and methods of delivering adhesive material are described for occluding target locations within a patient. The systems include a catheter configured to deliver adhesive to a target location and one or more of a light source to harden the adhesive, a retention structure to contain the adhesive prior to curing, a balloon to occupy a target location, and an open cell foam plug to occupy a target location.

18 Claims, 20 Drawing Sheets

Related U.S. Application Data

(60) Provisional application No. 62/511,214, filed on May 25, 2017.

(51) Int. Cl.
 *A61B 17/30* (2006.01)
 *A61B 90/00* (2016.01)
 *A61B 90/30* (2016.01)

(52) U.S. Cl.
 CPC .............. *A61B 2017/00734* (2013.01); *A61B 2017/00867* (2013.01); *A61B 2017/00893* (2013.01); *A61B 2017/00951* (2013.01); *A61B 2017/12054* (2013.01); *A61B 2017/12063* (2013.01); *A61B 2017/12068* (2013.01); *A61B 2017/306* (2013.01); *A61B 2090/306* (2016.02); *A61B 2090/3966* (2016.02)

(56) References Cited

U.S. PATENT DOCUMENTS

| | | |
|---|---|---|
| 5,122,136 A | 6/1992 | Guglielmi et al. |
| 5,330,483 A | 7/1994 | Heaven et al. |
| 5,334,210 A | 8/1994 | Gianturco |
| 5,354,309 A | 10/1994 | Schnepp-Pesch et al. |
| 5,397,331 A | 3/1995 | Himpens et al. |
| 5,466,242 A | 11/1995 | Mori |
| 5,478,331 A | 12/1995 | Heflin et al. |
| 5,496,277 A | 3/1996 | Termin et al. |
| 5,499,995 A | 3/1996 | Teirstein |
| 5,514,093 A | 5/1996 | Ellis et al. |
| 5,632,761 A * | 5/1997 | Smith .................... A61B 90/50 600/207 |
| 5,662,711 A | 9/1997 | Douglas |
| 5,713,848 A | 2/1998 | Dubrul |
| 5,718,159 A | 2/1998 | Thompson |
| 5,725,552 A | 3/1998 | Kotula et al. |
| 5,741,333 A | 4/1998 | Frid |
| 5,769,816 A | 6/1998 | Barbut et al. |
| 5,814,062 A | 9/1998 | Sepetka et al. |
| 5,814,064 A | 9/1998 | Daniel et al. |
| 5,846,261 A | 12/1998 | Kotula et al. |
| 5,853,422 A | 12/1998 | Huebsch et al. |
| 5,861,003 A | 1/1999 | Latson et al. |
| 5,868,778 A | 2/1999 | Gershony et al. |
| 5,919,224 A | 7/1999 | Thompson et al. |
| 5,925,060 A | 7/1999 | Forber |
| 5,941,896 A | 8/1999 | Kerr |
| 5,944,738 A | 8/1999 | Amplatz et al. |
| 5,947,997 A | 9/1999 | Pavcnik et al. |
| 5,954,745 A | 9/1999 | Gertler et al. |
| 6,010,498 A | 1/2000 | Guglielmi |
| 6,019,786 A | 2/2000 | Thompson |
| 6,022,336 A | 2/2000 | Zadno-Azizi et al. |
| 6,024,754 A | 2/2000 | Engelson |
| 6,027,520 A | 2/2000 | Tsugita et al. |
| 6,059,814 A | 5/2000 | Ladd |
| 6,066,149 A | 5/2000 | Samson et al. |
| 6,113,641 A | 9/2000 | Leroy et al. |
| 6,142,987 A | 11/2000 | Tsugita |
| 6,152,144 A | 11/2000 | Lesh et al. |
| 6,176,873 B1 | 1/2001 | Ouchi |
| 6,346,117 B1 | 2/2002 | Greenhalgh |
| 6,355,051 B1 | 3/2002 | Sisskind et al. |
| 6,375,668 B1 | 4/2002 | Gifford et al. |
| 6,379,329 B1 | 4/2002 | Naglreiter et al. |
| 6,428,557 B1 | 8/2002 | Hilaire |
| 6,428,558 B1 | 8/2002 | Jones et al. |
| 6,451,048 B1 | 9/2002 | Berg et al. |
| 6,468,303 B1 | 10/2002 | Amplatz et al. |
| 6,550,177 B1 | 4/2003 | Epple, Jr. |
| 6,585,748 B1 | 7/2003 | Jeffree |
| 6,589,265 B1 | 7/2003 | Palmer et al. |
| 6,652,555 B1 | 11/2003 | VanTassel et al. |
| 6,802,851 B2 | 10/2004 | Jones et al. |
| 6,811,560 B2 | 11/2004 | Jones et al. |
| 6,953,472 B2 | 10/2005 | Palmer et al. |
| 6,994,717 B2 | 2/2006 | Kónya et al. |
| 7,083,632 B2 | 8/2006 | Avellanet et al. |
| 7,122,058 B2 | 10/2006 | Levine et al. |
| 7,195,636 B2 | 3/2007 | Avellanet et al. |
| 7,229,461 B2 | 6/2007 | Chin et al. |
| 7,267,694 B2 | 9/2007 | Levine et al. |
| 7,294,146 B2 | 11/2007 | Chew et al. |
| 7,306,624 B2 | 12/2007 | Yodfat et al. |
| 7,320,065 B2 | 1/2008 | Gosior et al. |
| 7,326,224 B2 | 2/2008 | Houde et al. |
| 7,329,285 B2 | 2/2008 | Levine et al. |
| 7,569,066 B2 | 8/2009 | Gerberding et al. |
| 7,632,291 B2 | 12/2009 | Stephens et al. |
| 7,645,259 B2 | 1/2010 | Goldman |
| 7,665,466 B2 | 2/2010 | Figulla et al. |
| 7,678,129 B1 | 3/2010 | Gesswein et al. |
| 7,691,124 B2 | 4/2010 | Balgobin |
| 7,695,488 B2 | 4/2010 | Berenstein et al. |
| 7,713,282 B2 | 5/2010 | Frazier et al. |
| 7,749,238 B2 | 7/2010 | Corcoran et al. |
| 7,762,943 B2 | 7/2010 | Khairkhahan |
| 7,981,151 B2 | 7/2011 | Rowe |
| 8,034,061 B2 | 10/2011 | Amplatz et al. |
| 8,043,326 B2 | 10/2011 | Hancock et al. |
| 8,060,183 B2 | 11/2011 | Leopold et al. |
| 8,062,251 B2 | 11/2011 | Goldman |
| 8,066,732 B2 | 11/2011 | Paul et al. |
| 8,083,792 B2 | 12/2011 | Boucher et al. |
| 8,142,456 B2 | 3/2012 | Rosqueta et al. |
| 8,152,833 B2 | 4/2012 | Zaver et al. |
| 8,251,948 B2 | 8/2012 | Goldman |
| 8,262,719 B2 | 9/2012 | Erickson et al. |
| 8,280,486 B2 | 10/2012 | Miller et al. |
| 8,308,752 B2 | 11/2012 | Tekulve |
| 8,313,505 B2 | 11/2012 | Amplatz et al. |
| 8,352,014 B2 | 1/2013 | Leipold et al. |
| 8,357,180 B2 | 1/2013 | Feller, III et al. |
| 8,361,111 B2 | 1/2013 | Widomski et al. |
| 8,361,138 B2 | 1/2013 | Adams |
| 8,398,670 B2 | 3/2013 | Amplatz et al. |
| 8,408,212 B2 | 4/2013 | O'Brien et al. |
| 8,425,548 B2 | 4/2013 | Connor |
| 8,433,391 B2 | 4/2013 | Mark |
| 8,442,623 B2 | 5/2013 | Nicoson et al. |
| 8,454,633 B2 | 6/2013 | Amplatz et al. |
| 8,460,366 B2 | 6/2013 | Rowe |
| 8,480,702 B2 | 7/2013 | Kusleika et al. |
| 8,491,612 B2 | 7/2013 | Stopek et al. |
| 8,523,940 B2 | 9/2013 | Richardson et al. |
| 8,636,760 B2 | 1/2014 | Garcia et al. |
| 8,663,301 B2 | 3/2014 | Riina et al. |
| 8,671,815 B2 | 3/2014 | Hancock et al. |
| 8,679,150 B1 | 3/2014 | Janardhan et al. |
| 8,685,055 B2 | 4/2014 | VanTassel et al. |
| 8,690,907 B1 | 4/2014 | Janardhan et al. |
| 8,696,701 B2 | 4/2014 | Becking et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,715,338 B2 | 5/2014 | Frid |
| 8,721,676 B1 | 5/2014 | Janardhan et al. |
| 8,721,677 B1 | 5/2014 | Janardhan et al. |
| 8,721,707 B2 | 5/2014 | Boucher et al. |
| 8,728,112 B2 | 5/2014 | Evert et al. |
| 8,728,116 B1 | 5/2014 | Janardhan et al. |
| 8,728,117 B1 | 5/2014 | Janardhan et al. |
| 8,728,141 B2 | 5/2014 | Riina et al. |
| 8,733,618 B1 | 5/2014 | Janardhan et al. |
| 8,734,483 B2 | 5/2014 | Tekulve et al. |
| 8,735,777 B1 | 5/2014 | Janardhan et al. |
| 8,747,432 B1 | 6/2014 | Janardhan et al. |
| 8,747,453 B2 | 6/2014 | Amplatz et al. |
| 8,747,462 B2 | 6/2014 | Hill et al. |
| 8,747,597 B2 | 6/2014 | Rosqueta et al. |
| 8,753,371 B1 | 6/2014 | Janardhan et al. |
| 8,758,426 B2 | 6/2014 | Hood et al. |

(56) References Cited

U.S. PATENT DOCUMENTS

| | | |
|---|---|---|
| 8,764,772 B2 | 7/2014 | Tekulve |
| 8,764,787 B2 | 7/2014 | Ren |
| 8,777,974 B2 | 7/2014 | Amplatz et al. |
| 8,777,979 B2 | 7/2014 | Shrivastava et al. |
| 8,778,008 B2 | 7/2014 | Amplatz et al. |
| 8,783,151 B1 | 7/2014 | Janardhan et al. |
| 8,784,446 B1 | 7/2014 | Janardhan et al. |
| 8,789,452 B1 | 7/2014 | Janardhan et al. |
| 8,790,365 B1 | 7/2014 | Janardhan et al. |
| 8,795,316 B2 | 8/2014 | Balgobin et al. |
| 8,795,319 B2 | 8/2014 | Ryan et al. |
| 8,795,330 B1 | 8/2014 | Janardhan et al. |
| 8,803,030 B1 | 8/2014 | Janardhan et al. |
| 8,813,625 B1 | 8/2014 | Janardhan |
| 8,816,247 B1 | 8/2014 | Janardhan et al. |
| 8,821,529 B2 | 9/2014 | Kariniemi et al. |
| 8,821,849 B2 | 9/2014 | Schwartz |
| 8,828,043 B2 | 9/2014 | Chambers |
| 8,828,045 B1 | 9/2014 | Janardhan et al. |
| 8,828,051 B2 | 9/2014 | Javois et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,876,849 B2 | 11/2014 | Kratzberg et al. |
| 8,882,787 B2 | 11/2014 | Brenzel et al. |
| 8,882,797 B2 | 11/2014 | Janardhan et al. |
| 8,895,891 B2 | 11/2014 | Janardhan et al. |
| 8,900,287 B2 | 12/2014 | Amplatz et al. |
| 8,904,914 B2 | 12/2014 | Janardhan et al. |
| 8,905,961 B2 | 12/2014 | Braido et al. |
| 8,906,057 B2 | 12/2014 | Connor et al. |
| 8,910,555 B2 | 12/2014 | Janardhan et al. |
| 8,945,170 B2 | 2/2015 | Paul, Jr. |
| 9,011,476 B2 | 4/2015 | Sideris |
| 9,295,571 B2 | 3/2016 | Newell et al. |
| 9,579,104 B2 | 2/2017 | Beckham et al. |
| 9,770,234 B2 | 9/2017 | Sideris et al. |
| 10,398,441 B2 | 9/2019 | Warner et al. |
| 10,405,866 B2 | 9/2019 | Chakraborty et al. |
| 10,751,182 B2 | 8/2020 | Sutherland et al. |
| 10,952,740 B2 * | 3/2021 | Dasnurkar ......... A61B 17/1214 |
| 2001/0000797 A1 | 5/2001 | Mazzochi |
| 2001/0012949 A1 | 8/2001 | Forber |
| 2002/0042628 A1 | 4/2002 | Chin et al. |
| 2002/0082638 A1 | 6/2002 | Porter et al. |
| 2002/0111647 A1 | 8/2002 | Khairkhahan et al. |
| 2002/0123759 A1 | 9/2002 | Amplatz |
| 2002/0143349 A1 | 10/2002 | Gifford, III et al. |
| 2002/0156499 A1 | 10/2002 | Konya et al. |
| 2002/0165572 A1 | 11/2002 | Saadat |
| 2002/0189727 A1 | 12/2002 | Peterson |
| 2003/0023299 A1 | 1/2003 | Amplatz et al. |
| 2003/0199919 A1 | 6/2003 | Palmer et al. |
| 2003/0167068 A1 | 9/2003 | Amplatz |
| 2003/0220666 A1 | 11/2003 | Mirigian et al. |
| 2004/0044361 A1 | 3/2004 | Frazier et al. |
| 2004/0049210 A1 | 3/2004 | Vantassel et al. |
| 2004/0193206 A1 | 9/2004 | Gerberding et al. |
| 2005/0065484 A1 | 3/2005 | Watson |
| 2005/0070952 A1 | 3/2005 | Devellian |
| 2005/0228434 A1 | 10/2005 | Amplatz et al. |
| 2005/0234543 A1 | 10/2005 | Glaser et al. |
| 2005/0288706 A1 | 12/2005 | Widomski et al. |
| 2006/0135947 A1 | 6/2006 | Soltesz et al. |
| 2006/0161110 A1 | 7/2006 | Lenker et al. |
| 2006/0206139 A1 | 9/2006 | Tekulve |
| 2006/0241690 A1 | 10/2006 | Amplatz et al. |
| 2006/0247680 A1 | 11/2006 | Amplatz et al. |
| 2007/0055302 A1 | 3/2007 | Henry et al. |
| 2007/0066993 A1 | 3/2007 | Kreidler |
| 2007/0112380 A1 | 5/2007 | Figulla et al. |
| 2007/0135826 A1 | 6/2007 | Zaver et al. |
| 2007/0167980 A1 | 7/2007 | Figulla et al. |
| 2007/0179520 A1 | 8/2007 | West |
| 2007/0233186 A1 | 10/2007 | Meng |
| 2007/0239192 A1 | 10/2007 | Litzenberg et al. |
| 2007/0270891 A1 | 11/2007 | McGuckin, Jr. |
| 2008/0033480 A1 | 2/2008 | Hardert |
| 2008/0097495 A1 | 4/2008 | Feller, III et al. |
| 2008/0103585 A1 | 5/2008 | Monstadt et al. |
| 2008/0119887 A1 | 5/2008 | Que et al. |
| 2008/0249562 A1 | 10/2008 | Cahill |
| 2008/0262518 A1 | 10/2008 | Freudenthal |
| 2008/0281350 A1 | 11/2008 | Sepetka et al. |
| 2008/0306504 A1 | 12/2008 | Win et al. |
| 2009/0018562 A1 | 1/2009 | Amplatz et al. |
| 2009/0062845 A1 | 3/2009 | Tekulve |
| 2009/0082803 A1 | 3/2009 | Adams et al. |
| 2009/0187214 A1 | 7/2009 | Amplatz et al. |
| 2009/0209855 A1 | 8/2009 | Drilling |
| 2009/0216263 A1 | 8/2009 | Tekulve |
| 2010/0010517 A1 | 1/2010 | Stopek et al. |
| 2010/0030200 A1 | 2/2010 | Strauss et al. |
| 2010/0106235 A1 | 4/2010 | Kariniemi et al. |
| 2010/0160847 A1 | 6/2010 | Braido et al. |
| 2010/0217313 A1 | 8/2010 | Raabe et al. |
| 2010/0318097 A1 | 12/2010 | Ferrera et al. |
| 2010/0324586 A1 | 12/2010 | Miles et al. |
| 2011/0040324 A1 | 2/2011 | McCarthy et al. |
| 2011/0046719 A1 | 2/2011 | Frid |
| 2011/0082491 A1 | 4/2011 | Sepetka et al. |
| 2011/0118776 A1 | 5/2011 | Chen et al. |
| 2011/0265943 A1 | 11/2011 | Rosqueta et al. |
| 2011/0276080 A1 | 11/2011 | Nigon |
| 2011/0295298 A1 | 12/2011 | Moszner |
| 2011/0301630 A1 | 12/2011 | Hendriksen et al. |
| 2012/0041472 A1 | 2/2012 | Tan et al. |
| 2012/0046683 A1 | 2/2012 | Wilson et al. |
| 2012/0143008 A1 | 6/2012 | Wilkins et al. |
| 2012/0172928 A1 | 7/2012 | Eidenschink et al. |
| 2012/0215152 A1 | 8/2012 | Levine et al. |
| 2012/0239066 A1 | 9/2012 | Levine et al. |
| 2012/0245668 A1 | 9/2012 | Kariniemi et al. |
| 2012/0330341 A1 | 12/2012 | Becking et al. |
| 2012/0330348 A1 | 12/2012 | Strauss et al. |
| 2013/0012979 A1 | 1/2013 | Amplatz et al. |
| 2013/0018413 A1 | 1/2013 | Oral et al. |
| 2013/0085521 A1 | 4/2013 | Lim |
| 2013/0138136 A1 | 5/2013 | Beckham et al. |
| 2013/0190798 A1 | 7/2013 | Kapadia |
| 2013/0211443 A1 | 8/2013 | Cragg et al. |
| 2013/0245667 A1 | 9/2013 | Marchand et al. |
| 2013/0274868 A1 | 10/2013 | Cox et al. |
| 2014/0172001 A1 | 6/2014 | Becking et al. |
| 2014/0172004 A1 | 6/2014 | De Canniere |
| 2014/0222132 A1 | 8/2014 | Boucher et al. |
| 2015/0374483 A1 | 12/2015 | Janardahn et al. |
| 2016/0192912 A1 | 7/2016 | Kassab et al. |
| 2016/0206419 A1 | 7/2016 | Hebert et al. |
| 2017/0042549 A1 | 2/2017 | Kaplan et al. |
| 2018/0338767 A1 | 11/2018 | Dasnurkar et al. |
| 2019/0328412 A1 | 10/2019 | Mazhar et al. |
| 2020/0015827 A1 | 1/2020 | Anderson et al. |
| 2021/0330333 A1 | 10/2021 | Gray et al. |

FOREIGN PATENT DOCUMENTS

| | | |
|---|---|---|
| EP | 1994887 A1 | 11/2008 |
| JP | 2003-529410 A | 10/2003 |
| JP | 2007-519498 A | 7/2007 |
| JP | 2008-536620 A | 9/2008 |
| JP | 2012-523943 A | 10/2012 |
| WO | WO 2000/072909 A1 | 12/2000 |
| WO | WO2001/030266 A1 | 5/2001 |
| WO | WO 2014/146001 A2 | 9/2004 |
| WO | WO2005/074814 A2 | 8/2005 |
| WO | WO2005/074814 A3 | 8/2005 |

(56) References Cited

FOREIGN PATENT DOCUMENTS

| WO | WO 2006/115689 A1 | 11/2006 |
| WO | WO 2010/123821 A1 | 10/2010 |
| WO | WO 2013/005195 A1 | 1/2013 |
| WO | WO2013/068466 A1 | 5/2013 |
| WO | WO 2014/144980 A1 | 9/2014 |
| WO | WO 2014/145005 A2 | 9/2014 |
| WO | WO 2020/093012 A1 | 5/2020 |

OTHER PUBLICATIONS

WIPO, U.S. International Search Authority, International Search Report and Written Opinion dated Aug. 24, 2018 in International Patent Application No. PCT/US2018/034750, 9 pages.

European Patent Office, Extended European Search Report dated Apr. 4, 2024 in European Patent Application No. 21797206.6, 6 pages.

* cited by examiner

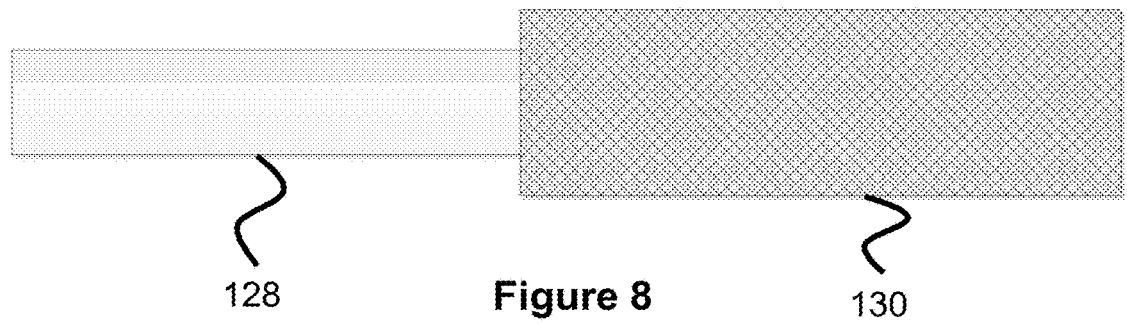
128  Figure 8  130
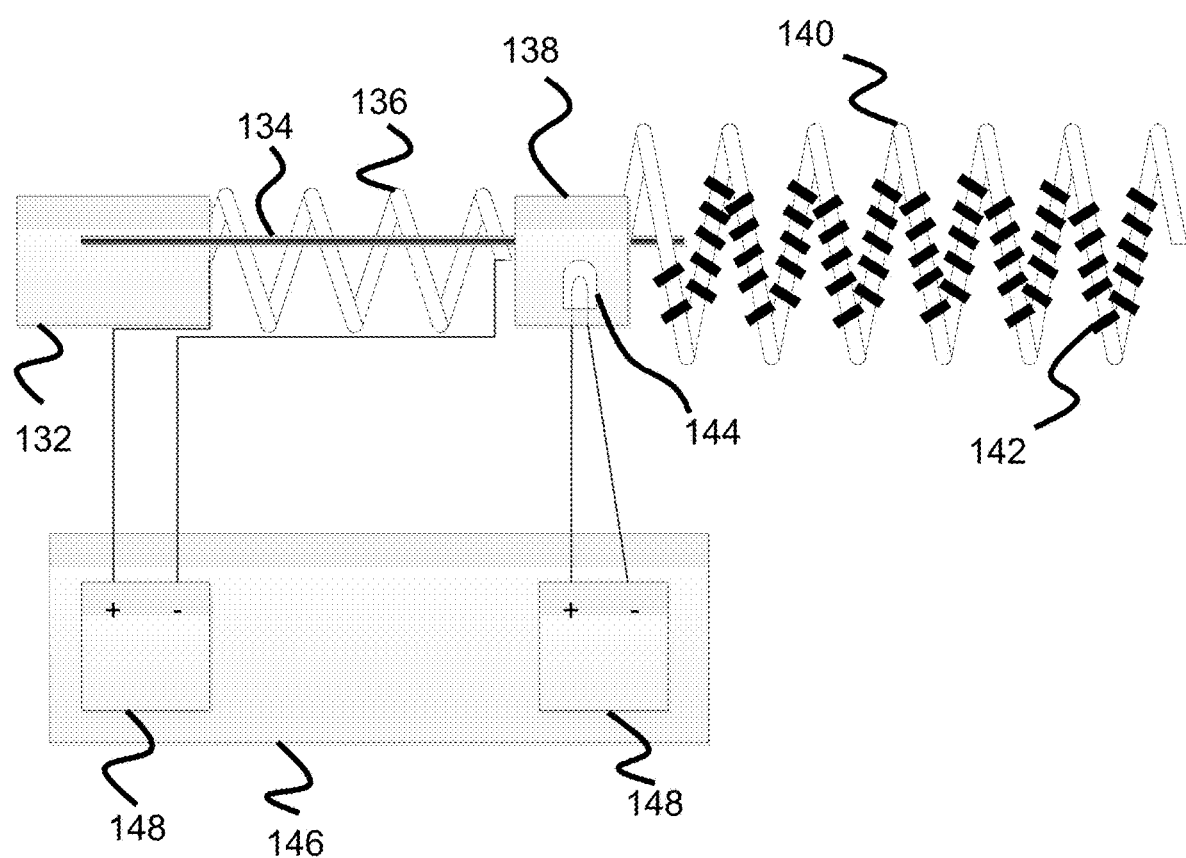
Figure 9A

ADHESIVE OCCLUSION SYSTEMS

RELATED APPLICATIONS

This application is a continuation of and claims priority to U.S. patent application Ser. No. 15/990,458 filed May 25, 2018 entitled Adhesive Occlusion Systems, which claims benefit of and priority to U.S. Provisional Application Ser. No. 62/511,214 filed May 25, 2017 entitled Methods and Devices Related to Treatment of Left Atrial Appendage, both of which are hereby incorporated herein by reference in their entireties.

BACKGROUND OF THE INVENTION

The invention deals with the field of embolic compositions used to occlude a treatment site to provide a therapeutic benefit, delivery systems for embolic compositions, and methods of delivering embolic compositions.

Embolic agents, including embolic coils, embolic meshes, tissue adhesives, and liquid embolics among other agents are used to occlude a target site within the vasculature. These agents can be used to treat a variety of conditions. A non-exhaustive list of conditions includes aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature.

Of these conditions, treatment of the left atrial appendage (LAA) can be particularly challenging since this small ear-shaped sac in the muscle wall of the left atrium is highly volatile and subject to high pulsation pressure due to its close proximity to the heart. For people with atrial fibrillation or irregular heartbeat, the heart impulse is irregular which can cause blood to collect in the LAA and clot over time. These clots can later migrate out of the LAA causing stroke issues.

Tissue adhesives are compositions which physically adhere to tissue. Tissue adhesives are typically used to seal vessel punctures. Some tissue adhesives are designed to harden upon exposure to light, including UV light. These compositions can be thought of as photopolymers which change properties when exposed to light, in a process known as curing. The compositions include a photo-initiator element which reacts with the adhesive upon exposure to light. Once exposed to light, constituent elements of the tissue-adhesive composition cross-link, resulting in a hardened composition which also adheres to tissue. The adhesive is delivered in a liquid or gel form to a treatment site, then exposed to light, and the adhesive then reacts by hardening or curing in response to bind to tissue. The compositions are typically hydrophobic and thus resist being washed away from blood. These light-activated adhesives are known as hydrophobic light-activated adhesive gels. Since these adhesives stick to the tissue, these systems can offer increased occlusive advantages since the solidified adhesive can fill a target space as well as adhere to the tissue—mitigating potential risk that the composition will flow out of the target treatment site.

Adhesive occlusive systems and/or adhesive occlusive delivery systems containing a light source that can be used to cross-link and harden a light-activated adhesive would be useful in order to occlude a treatment site. The occlusive systems could solely utilize a light-activated adhesive, or could utilize a light-activated adhesive along with additional occlusive or embolic compositions to occlude a treatment site. Such a system would augment occlusion since the occlusive formation would also adhere to tissue, creating a complete occlusive mass which is unlikely to migrate.

Adhesive occlusive systems that do not require light-activation to harden would also be useful in occluding a treatment site. However, due to the time necessary for these adhesives to harden, it can be difficult to maintain the liquid adhesive at the desired treatment site for the duration of the hardening/curing process.

There is a need for a device that can more effectively treat the above-mentioned conditions and especially left atrial appendage conditions.

SUMMARY OF THE INVENTION

An adhesive occlusion system is described. The system includes a catheter having a lumen used to deliver one or more embolic agents, where one of the embolic agents is a liquid or gel adhesive which cross-links and hardens and adheres to tissue upon exposure to light. The adhesive occlusion system includes a light source in order to activate the adhesive, and cause it to solidify and adhere with the tissue.

In one embodiment, the adhesive occlusion system utilizes a fiber optic member (such as an optical fiber or fiber optic cable) linking to the light source and an ultraviolet light as the light source.

In one embodiment, the adhesive occlusion system includes a single-lumen catheter. The lumen is used to deliver the adhesive gel, and the lumen also has an optical fiber or fiber optic cable therein. In another embodiment, the occlusive system includes a single-lumen catheter where an optical fiber or fiber optic cable sits outside of the catheter.

In one embodiment, the adhesive occlusion system includes a dual-lumen catheter. One lumen is used to deliver the adhesive, as well as other optional embolic agents. The second lumen includes an optical fiber or fiber optic cable which links to a light source used to activate a light-activated adhesive.

In one embodiment, the adhesive occlusion system includes a sealing structure at the distal portion of the catheter—in one embodiment, the sealing structure is configured to sit at the neck of the vascular condition to help seal the neck of the treatment site, and in another embodiment the sealing structure is configured to sit within the vascular condition. In one embodiment, the sealing structure is detachable.

In one embodiment, the adhesive occlusion system includes a catheter and a braided sealing structure near the distal portion of the catheter. Part of the braided sealing structure is comprised of optical fibers. The optical fibers link to a light source. Light-activated adhesive is delivered through the catheter to a treatment site. In one embodiment the braided sealing structure—comprising one or more optical fibers as part of the braid—sits near the neck of the treatment site and causes the light-activated adhesive to harden upon exposure to light; in another embodiment the braided sealing structure which includes one or more optical fibers sits within the treatment site. In some embodiments, the braided sealing structure can optionally be detached before the catheter is withdrawn from the treatment site.

In one embodiment, the adhesive occlusion system includes a catheter and a braided occlusive structure near the distal portion of the catheter. Part of the braided occlusive structure is comprised of optical fibers. The optical fibers link to a light source. Light-activated adhesive is delivered through the catheter to a treatment site. The braided occlusive structure—comprising one or more optical fibers as part of the braid—sits within the treatment site and causes the light-activated adhesive to harden upon exposure to light. In some embodiments, the braided occlusive structure can optionally be detached to occlude the target space before the catheter is withdrawn from the treatment site.

In one embodiment, the adhesive occlusion system includes an occlusive implant and a catheter. Part of the occlusive implant is comprised of optical fibers which are linked to a light source. The light-activated adhesive is first delivered to the treatment site, followed by the light-emitting occlusive implant. The light-activated adhesive hardens due to exposure to the light-emitting occlusive implant.

In one embodiment, the adhesive occlusion system includes a catheter which delivers light-curable adhesive and a light to activate the light-curable adhesive. In one embodiment, the light is placed on an external surface of the catheter. In another embodiment, the light is placed within a distal portion of the catheter. In another embodiment, the light is connected to a pusher member which is pushed through the catheter. The light includes an energy transmitting medium which can be placed externally or internally relative to the catheter. In one embodiment, the energy transmitting medium is a structural coil used to provide rigidity and strength to the catheter.

In one embodiment, an adhesive occlusion system includes a catheter having a radially expandable retention structure and an inflatable balloon that expands distally of the retention structure. The retention structure can be composed of a mesh braided from a plurality of wires and heat set to have an expanded configuration (e.g., a concave dish). The balloon can be either pre-coated with a tissue adhesive or can be inflated with a tissue adhesive that escapes from a plurality of ports/apertures near the distal end of the balloon. A detachable joint can be included to cause separation of the retention structure and balloon from the body of the catheter. In one embodiment, a valve is included that, once the catheter is separated, closes to prevent the escape of material proximally from the balloon and into the heart during an LAA occlusion procedure.

In one embodiment, an adhesive occlusion system includes a catheter having an open foam plug at its distal end. The plug may include a distal tether with an anchoring member at its end that secures the plug to tissue. The plug may also be either pre-coated with an adhesive or an adhesive passage within the catheter can be used to deliver the adhesive within the plug, so as to weep out to the plug's surface.

In one embodiment, an adhesive occlusion system includes a suction catheter that is used to adhere via suction to tissue within a LAA and then pull the tissue proximally to decrease the size of the LAA cavity. Adhesive delivery tubes are positioned adjacent the suction catheter to deliver adhesive within the LAA. An outer shield catheter may also be used to block of the opening of the LAA during the procedure.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 8 illustrates an embolic mesh and a delivery pusher, according to one embodiment.

FIG. 9a illustrates a delivery system for an embolic coil including a fiber optic member, according to one embodiment.

DESCRIPTION OF EMBODIMENTS

Figure 1:
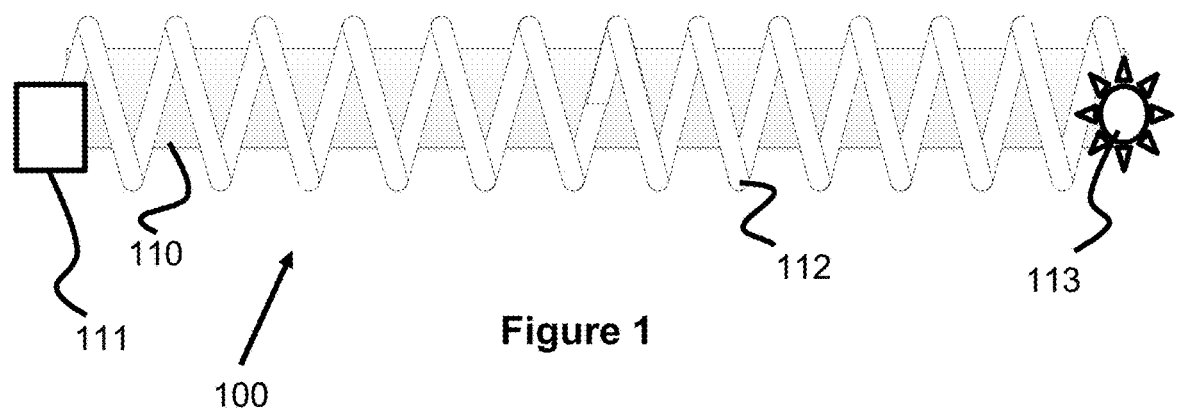
FIG. 1 illustrates a catheter including a fiber optic member, according to one embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

It should be explicitly noted that while numerous different specific embodiments are described herein, features, elements, and functionality of each can be incorporated into other embodiments shown. In other words, elements of the various embodiments are not intended to only be used with that specific embodiment, but can be "mixed-and-matched" with any of the other embodiments shown.

Occlusion is one technique used to address a number of intravascular issues, for example aneurysms and LAAs. With aneurysms, there is an abnormal bulging of a vessel wall and the rupture of the wall could lead to complications including stroke and death. Occlusion involves using a filling structure to either fill the intravascular structure or block flow to the intravascular structure (e.g., aneurysm) to cut off blood flow to the target region and prevent rupture. Currently, occlusion generally involves the use of embolic devices such as embolic coils to fill the structure. The use of embolic coils is problematic in two senses—the first is preventing coil migration where coils can migrate elsewhere and create a stroke risk elsewhere, and the second is creating a thrombogenic mass which sufficiently occludes the target region.

With LAAs, occlusion is particularly problematic. The LAA is a small ear-shaped sac in the muscle wall of the left atrium. For people with atrial fibrillation or irregular heartbeat, the heart impulse is irregular which can cause blood to collect in the LAA and clot over time. These clots can later migrate out of the LAA causing strokes. Presently, occlusion is one technique to treat this issue, and involves delivering an implant device within the LAA. However, designing an appropriate implant is difficult since the region is highly volatile and subject to high pulsation pressure due to its close proximity to the heart. To maximize anchoring force, these devices typically have barbs or other anchor mechanisms that penetrate the LAA tissue to maintain the position of the implant. However, these barbs cause tissue damage and even perforation, which can be undesirable for heart tissue.

Liquid embolics are a type of biocompatible glue which are delivered in a liquid form and harden within the vasculature to form a solidified mass and occlude a treatment site. Liquid embolics are currently used for a certain set of procedures, such as AVM (arterio-venous malformation) occlusion. It is difficult to use liquid embolics for a wide range of occlusive purposes, such as occluding aneurysms, since there is a risk of the embolic mass migrating prior to solidification—which could introduce additional risks such as stroke.

Tissue adhesives are adhesives which are delivered as a liquid or gel and solidify to bind tissue; tissue adhesives are often used for purposes such as wound repair and sealing vessel punctures. One advantage of tissue adhesives is that, unlike liquid embolic, tissue adhesives bind to the tissue itself thus forming a very firm occlusive mass which is unlikely to migrate. However, tissue adhesives are difficult to use for intravascular application since the adhesives can easily solidify prior to delivery, for example while being delivered through a delivery catheter. The ability for the adhesives to adhere to vessel tissue as well as occlude a treatment site means these adhesives can potentially be used for occlusive purposes—provided there is a way to control when solidification occurs and/or the location of the adhesives after delivery within the patient until solidification occurs. Various intravascular occlusive purposes could include, for example, aneurysms, atrial septal defects, patent foramen ovale, left atrial appendage occlusion (LAA), patent ductus arteriosus, fistula, arterio-venous malformations, fallopian tube occlusion for the purposes of sterilization, and occlusion in the peripheral vasculature where the adherence to vessel tissue augments the occlusive effect of these adhesives and makes it more likely the adhesive composition will stay within the target site and not migrate.

Recent advancements in tissue adhesives have seen the development of light-curable adhesives. Light-curable adhesives are adhesives which are delivered as a liquid or gel. Light-curable adhesives can go by a number of names, including HLAA (hydrophobic light-activated adhesive). The compositions include a photo-initiator element which reacts with the adhesive upon exposure to certain frequencies of light. Once exposed to light of a particular frequency range, constituent elements of the tissue-adhesive composition cross-link, resulting in a hardened composition which also adheres to tissue. These compositions can be thought of as photopolymers which change properties when exposed to light, here exposure to light causes cross-linking which results in the hardening of the adhesive composition. This property change can occur based on exposure to different frequencies of light, such as, in one example, UV light within a particular UV frequency range. These adhesive compositions are also generally hydrophobic and thus resist being displaced by blood. US20140348896 and WO15144898 disclose UV-curable adhesives and are hereby incorporated by reference in their entirety. PGSA (polyglycerol sebacate acrylate) is one such material that can be used as a biocompatible adhesive, it can be combined with a photo-initiator to create a hydrophobic light-activated adhesive gel which cross-links and hardens upon exposure to light.

Light-curable tissue adhesives are easily used for external or superficial wound repair since the light can easily be delivered to external wounds. However, when used within the vasculature, light-curable tissue adhesives can be pragmatically difficult to use since the tissue adhesive must first be delivered to the treatment site and then a light source must also be navigated to the treatment site. There could be a significant time lag between the placement of a light-curable tissue adhesive and the delivery of a curing light source, which could cause the tissue adhesive to migrate in the interim. The embodiments presented herein solve this problem by providing immediate light exposure to light-curable tissue adhesives, thereby allowing the tissue adhesives to solidify rapidly and create a firm occlusive mass which binds to tissue and can be used for a variety of intravascular occlusive purposes. In some embodiments, a delivery catheter used to deliver the light-curable adhesive also includes the light to cure said adhesive. In other embodiments, embolic devices which are delivered along with the light-curable adhesives also include the light to cure said adhesive.

When discussing light-curable adhesives, the adhesives are configured to cure based on exposure to particular frequencies of light. The specification will discuss light sources used within an adhesive delivery system, the light sources should be understood as sitting within an appropriate frequency range to cause curing of the light-activated adhesive. For instance, some adhesives are UV-curable where exposure to UV light within a particular frequency range will cause curing. The adhesive delivery system will, in turn, use a UV light which emits light within the particular frequency range to thus cure the light-activated adhesive. Alternatively, some adhesives cure or harden in response to exposure to a particular frequency range of "blue" light. The adhesive delivery system will, in turn, use a blue light within a particular frequency range to cure the light-activated adhesive. Please note, the curing effect is based on the chemical composition of the adhesive, so different frequency/color lights can also be used to affect curing of the adhesive.

FIG. 1 shows an occlusive adhesive delivery system according to one embodiment, which includes a catheter 110. The catheter 110 includes an open lumen spanning the length of catheter 110, and the catheter lumen is used to deliver light-curable adhesive as well as other optional additional embolic agents/devices. A cable 112, in one example a fiber optic cable and in another example an optical fiber, is wound and fixed to an outside surface of the catheter 110. A light source is attached to the proximal end of the cable; the light generated by the light source is conveyed through the cable to the distal end of the cable (e.g., to a lens 113) which sits at the distal end of the catheter. When the light-curable adhesive is delivered, it immediately reacts with the light from the fiber optic cable or optical fiber and quickly hardens.

Please note the specification may alternately refer to optical fibers, fiber optics, fiber optic cables. Optical fibers are generally the actual fibers that convey light. Fiber optic cables are bundles of these optical fibers placed within a cable. These terms, within the concept of the specification, can be used synonymously and broadly to refer to all the concepts. Thus, the term optical fiber should also envelop fiber optic cables. The term fiber optic cable should envelop optical fibers. The term fiber optic member can also be used to refer to both fiber optic cables and optical fibers. Other light-transmitting means are also possible, besides optical fibers and fiber optic cables and can be used with the principles espoused within.

One advantage of using an optical fiber or fiber optic cable to transmit light from a proximal light source is ease of design. A light source placed at the distal end of the catheter would require a proximal battery, and at least two wires which span the length of the catheter to connect the polarized terminals of the battery to the light source. On the other hand, with an optical fiber or fiber optic cable, a proximal assembly could contain the light source, and the fiber or cable would transmit the light to the distal end of the system. Since one optical fiber or one cable bundle could be used to transmit the light, just one fiber or cable could be used instead of two separate wires. In addition, where wires are used to convey electrons within a circuit path from a proximal battery to a distal light source, the degradation of a wire completely destroys the circuit and would cause the distal light to fail. With, for example, a fiber optic cable comprising a plurality of optical fibers, the failure of one optical fiber will still allow light to transmit since other optical fibers can still transmit the light.

Different embodiments can utilize the fiber optic cable or optical fiber in different locations of the catheter, for example the tubular wall of the catheter can contain the fiber optic cable or optical fiber. Coils or braids are often used to provide structural support and rigidity to catheters so they can be pushed through tortuous anatomy without kinking. The cable/fiber could be incorporated as part of the one or more coils and/or braids used to provide structural support to the catheter. Additionally, multiple cables/fibers could be used with one or more light sources to further augment the illumination at the distal end of the system.

Figure 2:
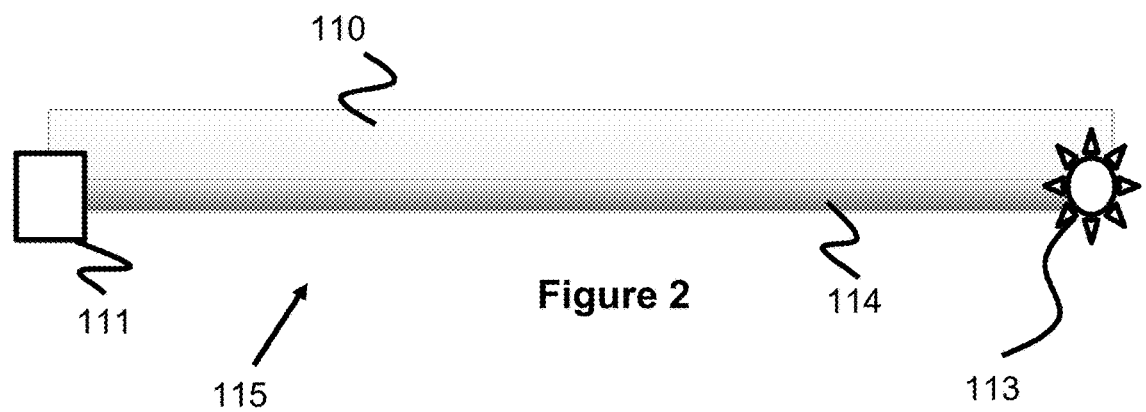
FIG. 2 illustrates a catheter including a fiber optic member, according to one embodiment.
Figure 3:
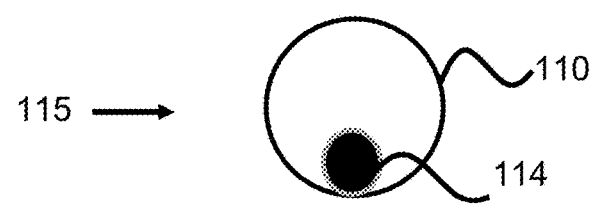
FIG. 3 illustrates a catheter including a fiber optic member, according to one embodiment.

FIGS. 2-3 shows an adhesive delivery system according to another embodiment, the system includes a catheter 110 where the cable 114 is housed within the catheter, here shown at the bottom of catheter 110 (although cable 114 could be placed anywhere within catheter 110). Cable 114 could also be wound around the inner lumen of catheter 110. In this embodiment, appropriate shielding would need to be placed around the cable to prevent the light from illuminating within the catheter which could cause premature curing as the light-activated embolic is delivered through the catheter—for instance, a blackened cable housing or additional cable shielding/cladding could be used to prevent illumination within the catheter. Higher frequencies of light could also contribute to heat generation, so shielding or cladding could also be used to limit heat dissipation within the catheter. Alternatively, cable 114 could be placed within the wall of catheter 110—in one example a cable sits longitudinally straight within this wall region, in another example the cable is coiled within this wall region (e.g., similar to the coiled shape of cable 112 in FIG. 1).

Figure 4:
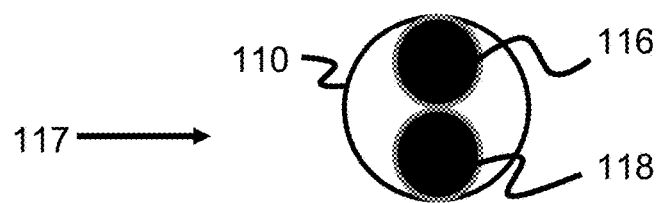
FIG. 4 illustrates a dual-lumen catheter where one lumen is used to deliver embolic and another lumen contains a fiber optic member, according to one embodiment.

FIG. 4 shows a catheter 110 according to another embodiment where the catheter 110 includes two lumens 116, 118. One lumen (e.g. lumen 116) is used to deliver the light-activated adhesive as well as other embolic material, while the other lumen (e.g. lumen 118) contains the cable connecting to the light source. Since early exposure to light is undesirable, a blackened cable housing or additional cable shielding/cladding could be used around the optical fibers or fiber optic cable to prevent the light-curable adhesive from being illuminated or otherwise exposed to heat during delivery through the catheter.

In one embodiment, the proximal end of the occlusive delivery system would contain a user control interface. The user control interface would include a light source, an optical fiber or fiber optic cable linked to the light source, and an energy source such as a battery to power the light and optionally power other necessary functions. The user interface would contain appropriate circuitry so the user could interact with the user control interface (i.e. push a button) to cause the light to light up. In other embodiments, the light at the proximal end of the system continuously shines and the cable would transmit the light, so the light would continuously shine at the distal end of the delivery system.

The cable or optical fibers should be thought of as an energy transmitting means to convey energy from the light source to the distal end of the device.

Figure 5:
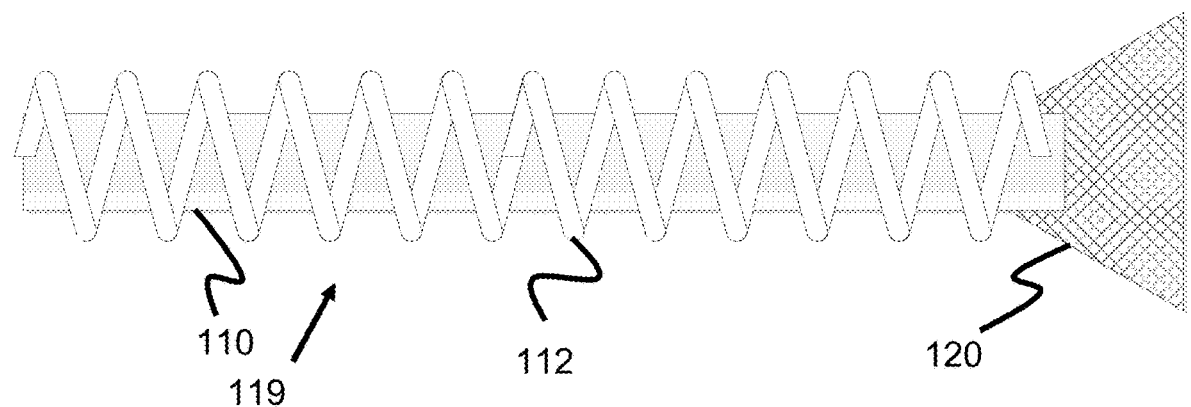
FIG. 5 illustrates a catheter including a sealing structure and a fiber optic member, according to one embodiment.

FIG. 5 shows another embodiment of an adhesive occlusive delivery system which includes a catheter 110 and a sealing structure 120 at the distal region of the catheter. In one embodiment, sealing structure 120 can be used as a neck seal which sits at the neck, opening, or ostium of the vascular condition (e.g. neck of aneurysm), where the sealing structure 120 would help ensure delivered embolic material does not seep out of the target region. In another embodiment, sealing structure 120 can be physically placed within the treatment site (e.g. aneurysm) and used to help ensure delivered embolic material does not seep out of the target region. The width of sealing structure 120 and its position relative to the distal end of catheter 110 are a couple of variables that would impact whether sealing structure 120 would function as a neck seal, or be placed within the treatment site.

Sealing structure 120 can be a wire or braid mesh comprised of one or more metallic wires. A fiber optic cable or optical fiber 122, similar to cable 112 shown in FIG. 1 spans the length of the catheter and continues into sealing structure 120 to define one of the constitute elements comprising the braid—in other words, the braid forming sealing structure 120 would comprise metallic wires as well as cables or optical fibers. Similar to the embodiment shown in FIG. 1 and discussed earlier, cable 122 can be incorporated as part of a coil or braid spanning the length of catheter 110 used for structural support of the catheter. Cable 122 continues into the sealing structure 120 mesh, and cable 122 in turn is one of the constituent wire elements making up the seal mesh. In one example, sealing structure 120 is a mesh composed of nitinol wires, and optionally can include radiopaque wires as well (i.e. platinum, platinum, or gold) to aid in visualization during the intravascular procedure. Cable 122 could thus be considered another constituent element of the mesh, along with the nitinol wires and optional radiopaque wires. Cable 122, as described earlier, is connected to a proximal light source and the light is conveyed through the cable to the distal end of the cable. Since the distal end of cable 122 is part of the sealing structure 120, the sealing structure 120 would in turn illuminate. Similar to the description above, the light source can either consistently emit light, or the user could take some action (i.e. press a button on a user interface) to cause the light source to light up when desired.

In one embodiment, sealing structure 120 is detachable. Thermal, mechanical, or electrolytic detachment means which are well known in the art be placed at the proximal end of the sealing structure 120 where said sealing structure 120 is connected to catheter 110. The user interface described earlier can also contain appropriate circuitry and an interface (i.e. button) to effect detachment of the sealing structure 120. In one example, a light-activated adhesive is delivered through the catheter to a target treatment site (i.e. an aneurysm or AVM). Additional embolic agents such as embolic coils or embolic meshes an also be delivered through the catheter into the target treatment site. Where the light is selectively emitted, the user can take an action (i.e. press a button) to cause the light to emit light, and the light is conveyed to the distal end of the device. Where the light is constantly emitted, the light will be consistently conveyed to the distal end of the device without any action needed. Exposure to the light will cause the light-activated adhesive to harden and thus occlude the target site. Sealing structure 120 can then optionally be detached to keep the embolic mass (the solidified adhesive, and any additional embolic agents such as embolic coils/embolic meshes) within the aneurysm. Alternatively, sealing structure 120 is not detached and the occlusive mass caused by the hardened adhesive and any additional embolic agents (e.g. embolic coils and/or embolic meshes) will fill the treatment site without dissipation, where catheter 110 and the associated sealing structure 120 are removed once it is confirmed that a sufficient embolic mass has formed. Detachability of sealing structure 120 is only a possible feature of the system and should not be considered necessary since the embolic formation should take place rather quickly once the light-curable adhesive is exposed to light.

In some embodiments, sealing structure 120 could function like an occlusive agent. Catheter 110 is placed within the treatment site, so that sealing structure 120 shown in FIG. 5 also sits within the treatment site (e.g. aneurysm). Light-curable adhesive delivered from the catheter reacts with the light emanating from the optical fibers in element 120 and hardens. The sealing structure 120 can then optionally be detached and catheter 110 can be withdrawn. Thus, sealing structure 120 would, in this case, act like an occluding agent rather than a neck seal since it's placed and detached within the aneurysm.

The light-activated adhesive is delivered as a liquid or gel via a syringe at the proximal end of the system, where the adhesive is delivered through the catheter 110. Catheter 110 is navigated through the vasculature to the target treatment location. The light-activated adhesive is then delivered via syringe, through the catheter, and to the target treatment location. The light-activated adhesive is then exposed to light and cures or hardens, thus occluding the treatment site. Additional embolic agents (e.g. embolic coils) can also be optionally delivered through the catheter either before or after delivery of the light-activated adhesive.

A balloon can optionally be placed near the treatment site to prevent adhesive dissipation prior to solidification due to light exposure. For example, where the light-curing adhesive is used to treat an aneurysm, a balloon can be placed across the neck of the aneurysm to prevent embolic dissipation before the embolic hardens. Catheter 110 would first be placed into the aneurysm, and a balloon would be placed and inflated under the neck of the aneurysm to seal the space, so adhesive cannot migrate out of the aneurysm prior to solidifying. This may be desirable where there might be a lag between the time that the light-sensitive adhesive is introduced into the treatment site and the time that the adhesive is exposed to light causing it to solidify. Sealing structure 120 would help keep the adhesive in the treatment site and keep it from migrating elsewhere. Other devices such as stents could also be used instead of a balloon, however, the stent should have a relatively tight barrier layer to help prevent dissipation of the adhesive and the adhesive should have relatively quick exposure to the curing light in order to prevent adhesive migration prior to solidification.

In other embodiments which will now be discussed, an occlusive implant functions as the light source to activate the light-curable adhesive. Occlusive implants such as embolic coils are currently used for occlusive purposes, the coils adopt various shapes upon delivery and fill the treatment site (i.e. aneurysm). In the embodiments of the present invention utilizing an occlusive implant as a light source, a light-activated adhesive is initially delivered through a catheter. After delivery, a light-emitting occlusive implant is delivered to the target treatment site. The adhesive hardens after being exposed to the light-emitting occlusive implant and the occlusive implant and hardened adhesive then comprise the occlusive formation which occludes the target treatment site. A balloon or stent can optionally be placed near the treatment site (i.e. under the neck of an aneurysm) to prevent adhesive and other embolic agents from flowing out of the treatment site before hardening.

Figure 6:
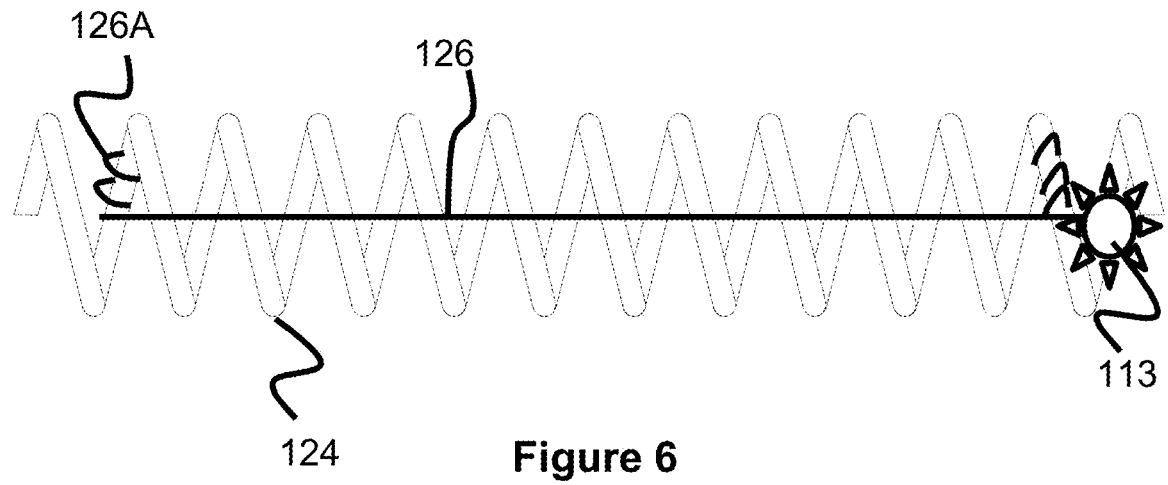
FIG. 6 illustrates an embolic coil including a fiber optic member, according to one embodiment.

FIG. 6 shows an embodiment of a light-emitting occlusive implant, shown as an embolic coil 124. Embolic coil 124 can be made of various materials including polymer, platinum, platinum-tungsten, nitinol, stainless steel, cobalt chromium, or combinations therein. Embolic coil 124 includes a fiber optic element 126, in the figure the fiber optic component is shown as being tied along various loops of the coil so that the fiber optic component is substantially taut and sits in the lumen defined by the coiled lumen of the coil. The fiber optic component 126 can also be helically wound around the surface of the coil.

The occlusive implant could also adopt other configurations in different embodiments, in lieu of embolic coil 124. In one embodiment, the light-emitting occlusive implant could be a braided mesh where the mesh is comprised of various metallic wires—for instance, nitinol and platinum wires. Intrasaccular devices are devices which conform to the shape of the treatment region (e.g. aneurysm) and are often composed of soft occlusive meshes which are highly conformable so as to adopt to the shape of the target region. Occlusive meshes and intrasaccular devices are described in US20140200647, which is hereby incorporated by reference in its entirety. In these embodiments, the light emitting occlusive mesh could be thought of as an intrasaccular device. An optical fiber is also included in the mesh in order to allow the mesh to emit light.

Occlusive implants typically include a pusher element used to push the occlusive device through the catheter, and a severing means used to sever the occlusive implant from the pusher and deposit the occlusive implant within the target space. Mechanical, thermal, and electrolytic means are typically used to sever the occlusive implant from the pusher. An attachment component such as a degradable linkage (i.e. tether or adhesive) can connect between the occlusive device and the pusher, and degradation of this linkage allows the occlusive device to detach from the pusher. US20100269204, US20110301686, US20150289879 all describe thermal detachment systems and are hereby incorporated by reference in their entirety as examples of thermal detachment systems that could be used to detach the occlusive implant from the pusher.

Figure 7:
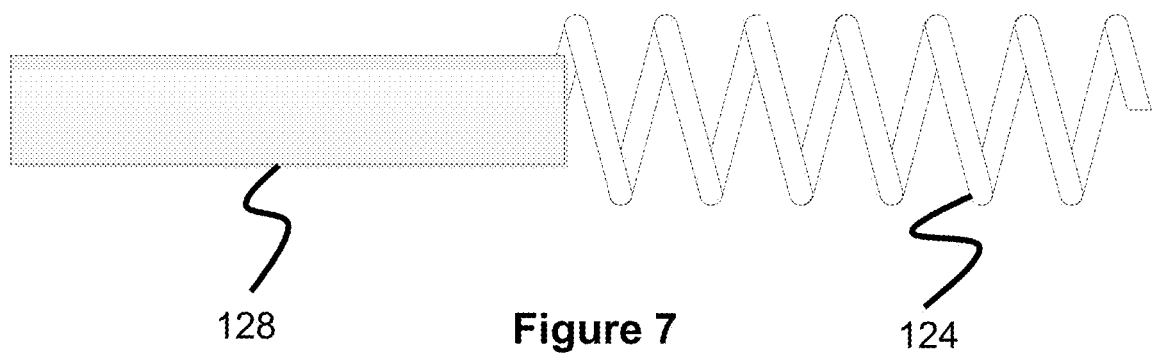
FIG. 7 illustrates an embolic coil and delivery pusher, according to one embodiment.

FIGS. 7-8 show a pusher 128 connected either to an embolic coil 124 or an embolic mesh 130. The embolic coil or embolic mesh includes an optical fiber member (not shown). The inclusion of the optical fiber as part of the embolic coil or embolic mesh was discussed earlier. The optical fiber member would allow the embolic coil or mesh to be lit, as discussed earlier.

The principle of the concepts discussed and described so far in FIGS. 6-8 is that the occlusive devices should be lit so that when the occlusive device is delivered to the treatment site, the light from the occlusive device reacts with the light-curable adhesive and causes the adhesive to solidify. FIG. 9a illustrates such an embodiment. A pusher system 132 is used to deliver an embolic coil 140. A heater coil 136 is placed near the distal end of the pusher, and a severable tether 134 extends within the heater coil. A hypotube element 138 sits distal of the heater coil and includes a light element 144. An embolic coil 140 sits distal of hypotube structure 138 and the embolic coil includes an optical fiber component 142. The optical fiber component 142 can be wound around the embolic coil (as represented in FIG. 9) or can be tied within and along the length of the embolic coil.

Light element 144 sits proximal of optical fiber 142 and when the light element is lit, light passes through optical fiber 142 and is emitted at the distal end of optical fiber 142. Hypotube element 138 can be coated to reduce dissipation of the light and/or be made of a material to maximize reflection and minimize absorption so most of the generated light is passed to the optical fiber. A user interface 146 is at the proximal end of the system and includes voltage sources (shown as batteries 148). FIG. 9 shows two batteries, where one battery powers the heater coil 136 and another battery powers light element 144—however other variations could utilize one battery with a parallel circuit structure to power both the heater coil and light element. The user interface would include a means (i.e. one or more buttons) for the user to activate the heater coil and/or the light element. Heating the heater element 136 will sever tether 134, detaching the embolic coil 140. So, for example, the user could press a button to complete the circuit to send an impulse to the heater coil, which heats the heater coil, and results in tether 134 severing. Light element 144, in one embodiment, can be consistently lit meaning the optical fiber is continuously lit. In another embodiment, the user could press a button to light the light element to cause the optical fiber to pass and emit the light. In the embodiment of FIG. 9a, the light 144 would cease to function once the embolic coil 140 is detached, so in practice the user would push the lit coil out of the distal end of the catheter and use the illuminated coil to cure the adhesive. The user could then optionally detach the embolic coil where the embolic coil would also function as an occlusive implant, however, once the embolic coil is detached it would cease to emit light.

Figure 9B:
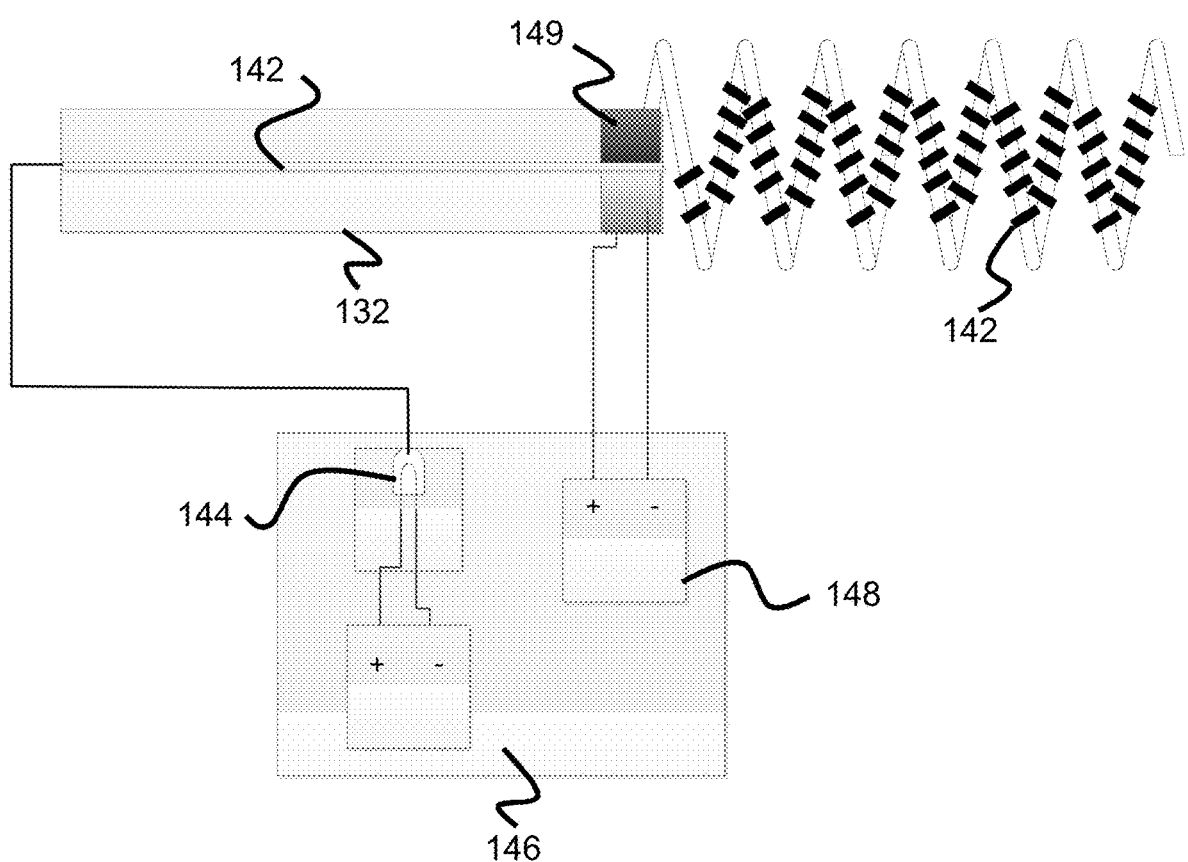
FIG. 9b illustrates a delivery system for an embolic coil including a fiber optic member, according to one embodiment.

A variation of this embodiment is shown in FIG. 9b, here the main difference is that the user interface 146 includes a light 144. The proximal end of pusher member 132 can be placed within the user interface to establish electrical communication between the pusher 132 and the user interface 146. The pusher includes an optical fiber or fiber optic cable 142, in one example cable 142 sits within the interior of the pusher as shown in FIG. 9b and in another example the cable is wound around the periphery of pusher 132. Cable 142 traverses past the pusher and is either wound around the surface of embolic coil 140 or tied to embolic coil 140. When the proximal end of pusher 132 is connected to user interface 146, the light from the user interface 146 is transmitted through cable 142 to embolic coil 140 to light the embolic coil. A sacrificial joint 149 is located between the pusher 132 and embolic coil 142 and can be degraded via thermal, mechanical, or electrolytic means in order to sever the embolic coil 142 from pusher 132 in order to deliver said embolic coil 142.

Figure 9C:
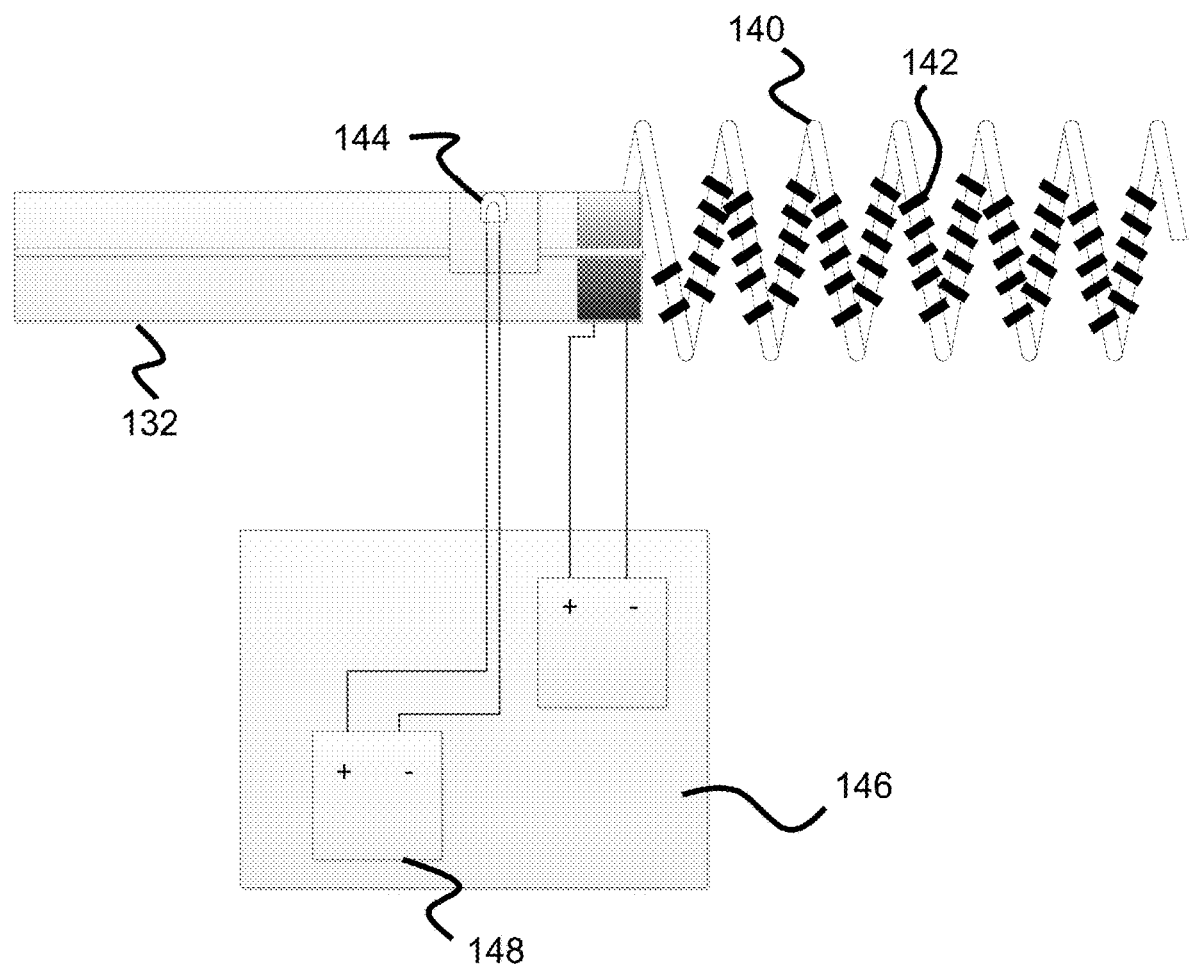
FIG. 9c illustrates a delivery system for an embolic coil including a fiber optic member, according to one embodiment.

FIG. 9c shows another variation of this embodiment, utilizing a light 144 within pusher 132, where the light within the pusher conveys light to the optical fiber component 142 to light the embolic coil 140.

In one embodiment, light-activated adhesive would first be delivered through the catheter. The embolic coil delivered from pusher 132 is then delivered through the catheter. When the light element 144 is lit, and the embolic coil sits near the distal end of the catheter or is pushed out of the distal end of the catheter, the light reacts with the light-activated adhesive to cause it to harden. The embolic coil can be pushed completely out of the catheter so the distal end of pusher 132 is flush near the distal end of the catheter. The user can then detach the embolic coil by activating heater 136 to sever tether 134, detaching the coil within the target treatment site. Note that once the coil is detached, the optical fiber is no longer emitting light since the optical fiber ferries light generated from light element 144, so once the embolic coil is detached from the pusher (which also detaches it from hypotube 138 which contains pusher light element 144), there is no connection between the coil/optical fiber and light element 144. In other embodiments, the optical fiber containing embolic coil can solely be used to harden the light-activated adhesive, so the user could just use the light from the optical fiber to react with the adhesive but not detach the coil. Thus, the coil could be placed flush or external to the distal tip of the catheter, and used to cure the adhesive, and then be withdrawn without being detached.

Other embodiments could utilize a dual-lumen catheter system, like the dual-lumen system showed in FIG. 4 where a first lumen (e.g. lumen 116) is used to deliver a light-emitting occlusive coil and a second lumen (e.g. lumen 118) is used to deliver a light-curable adhesive. A dual-lumen catheter system would allow a light-emitting occlusive coil to be delivered prior to a light-curable adhesive such that the light-curable adhesive is immediately cured upon delivery. In one embodiment, a light-emitting occlusive coil is pushed past the distal end of a first lumen of the catheter but not detached—such that the occlusive coil is still connected to the pusher. A light-curable adhesive is then delivered through a second lumen of the catheter, the adhesive is exposed to the light-emitting occlusive coil which cures the adhesive upon delivery. The occlusive coil could then optionally be subsequently detached.

Figure 10:
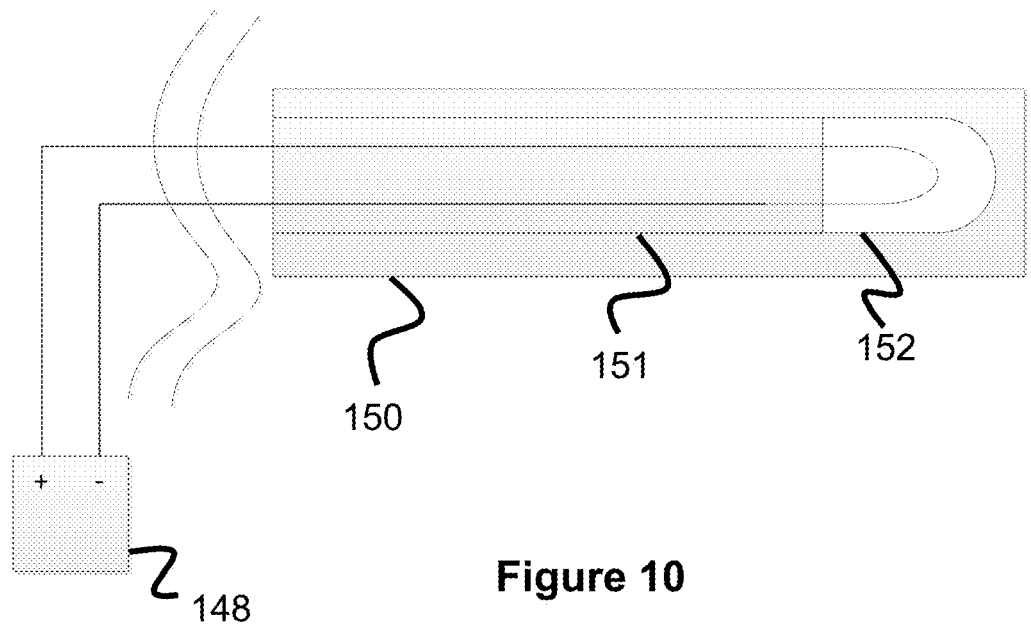
FIG. 10 illustrates a pusher with a light element, according to one embodiment.
Figure 11:
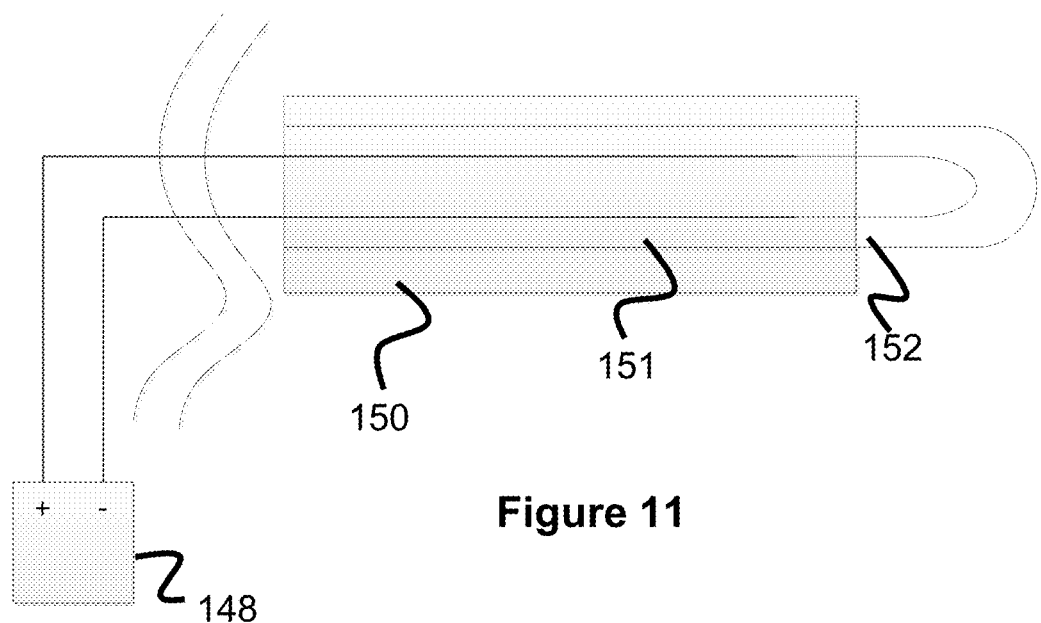
FIG. 11 illustrates a pusher with a light element, according to one embodiment.

Other embodiments could utilize a pusher member with a light at the distal end of the pusher member used to cure the light-activated adhesive. In these embodiments, the light-activated adhesive would first be delivered through the catheter. A pusher with a light at the distal end of the pusher would then be tracked through and past the distal end of the catheter, and the light reacts with the adhesive to cure and harden it. This is shown in FIGS. 10-11 where a pusher 151 is tracked through a catheter 150 and pusher 151 has a light element 152 at its distal end. The light element is pushed outside of the catheter and reacts with the light-adhesive. The light source has a voltage source to power it, shown as a battery 148 and the pusher can contain the appropriate wiring to connect the battery and the light element. Other embodiments could utilize a dual-lumen catheter as shown in FIG. 4 where a first lumen is used to deliver a light-activated adhesive and a second lumen is used to deliver the pusher member with distal light. The advantage of a dual lumen system is that the pusher could be pre-delivered to the distal tip of the catheter, and the light-activated adhesive would immediately react and cure due to exposure to the light upon delivery—mitigating the risk of the adhesive dissipating prior to solidification and possibly avoiding the need to use a balloon around the target treatment site (e.g. under the neck of an aneurysm) to prevent adhesive dissipation prior to solidification.

Figure 12:
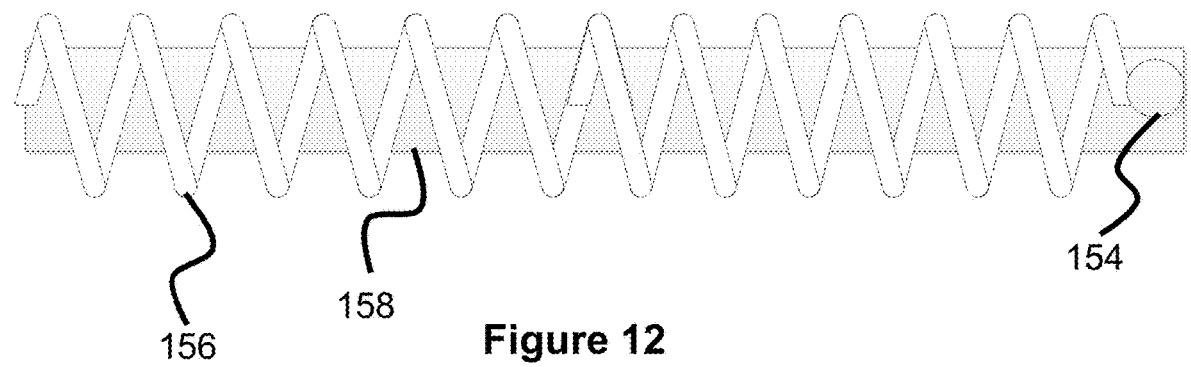
FIG. 12 illustrates a catheter with a light element, according to one embodiment.

FIG. 12 shows another embodiment of an adhesive delivery system where a light can be mounted to the catheter itself, and the light is used to cure light-activated adhesive. The previous embodiments utilized a proximal light source and a fiber optic member to deliver the light to a distal region of the catheter—in contrast, the embodiment of FIG. 12 utilizes a light source 154 placed in a distal region of the catheter 158. The light-activated adhesive is delivered through the catheter and reacts with the catheter-mounted light to cure and harden the adhesive. Instead of wiring connecting to the light source, a metallic coil or metallic braid 156 which is used to provide structural rigidity and support to the catheter can also be used to ferry current to the light source. In this embodiment, two coil elements (one supply, one return) can be used. Alternatively, one coil element can be used (i.e. for the supply) and the blood itself can comprise the ground to complete the circuit to power the light. The coil(s) could be placed externally of the catheter tubing (as shown), or be placed within the wall of the catheter tubing. In alternative configurations, similar concepts to FIGS. 2-4 could be used where one or more wires are placed within the catheter to power the light, or a multi-lumen catheter which includes a separate lumen for the wires powering the light could also be used. In these configurations all the circuitry would be within the catheter, but the light would be mounted externally of the catheter. Alternative configurations could utilize a thin or small-profile light which sits within the catheter—the light should be small enough to not block the catheter lumen, however the light should be radiant enough to cure the light-activated adhesive. Other configurations could utilize multiple lights. A proximal user interface connecting the wires or coil components could utilize a battery to power the device, and a push-button to toggle the light on or off.

Figure 13:
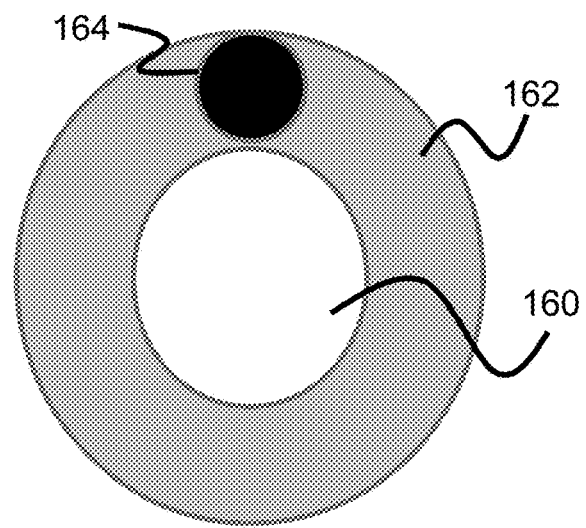
FIG. 13 illustrates a catheter with a light element embedded within the wall of the catheter, according to one embodiment.

FIG. 13 shows another embodiment utilizing a light 164 where the light is integrated into the wall 162 of a catheter. The catheter contains a lumen 160 used to deliver the light-curable adhesive, and the adhesive is exposed to the light 164 upon delivery and cures. Other embodiments could utilize a proximal light source and an optical fiber or fiber optic cable placed within the wall of the catheter, where the distal end of the fiber optic component is exposed to cure the adhesive. Other embodiments could utilize multiple lights within wall region 162 or multiple optical fibers/fiber optic cables within wall region 162.

The following embodiments would be useful for treating a variety of vascular conditions but have special utility in treating left atrial appendage (LAA) as well as some types of aneurysms. An LAA is a small ear-shaped sac in the muscle wall of the left atrium, patients with atrial fibrillation or irregular heartbeat are at risk of clots forming in the LAA which can cause complications such as stroke if these clots are pumped out of the heart and migrate elsewhere. Occlusion of the LAA is one technique that is practiced to prevent this situation for patients with irregular heartbeat or atrial fibrillation. LAA's can adopt awkward, complex shapes which makes occlusion of the LAA difficult. Additionally, since the LAA is so close to the heart, the region is exposed to heavy pulsatile pressure which makes placement and retention of occlusive devices very difficult. Current devices to occlude LAA's typically utilize sharp barbs to help stay affixed within the LAA given the complex morphology and pulsatile pressure of the LAA space, however, these barbs can lead to other complications include bleedout between different vessels. The following embodiments utilize a light-curable adhesive to treat a variety of conditions, in particular aneurysms and LAA. Some of these embodiments utilize a pusher used to deliver a light used to cure a light-activated adhesive, similar to the embodiments shown in FIGS. 10-11.

Figure 14:
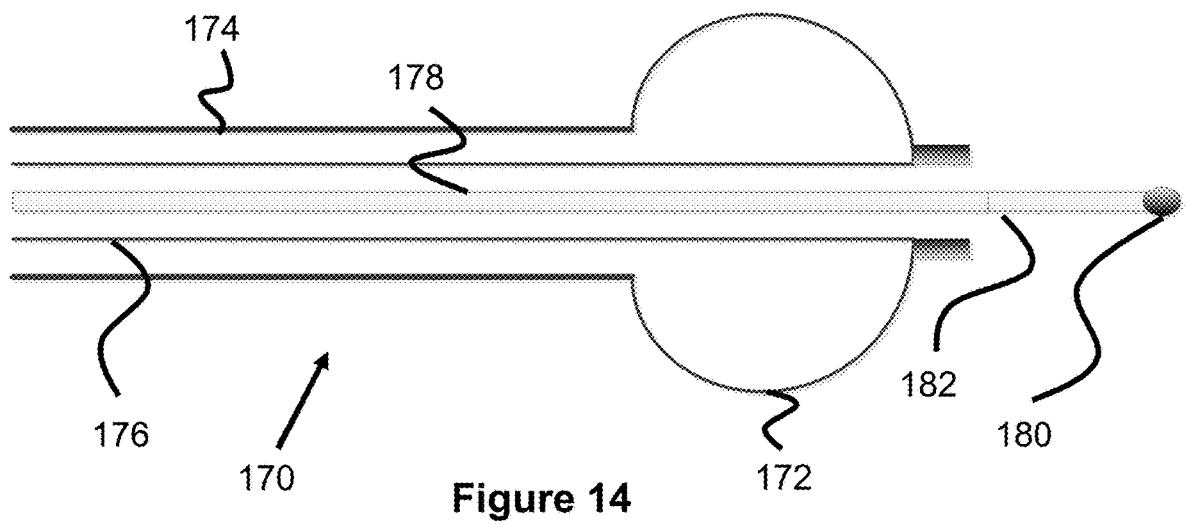
FIG. 14 illustrates a catheter with a light element, according to one embodiment.

In one embodiment shown in FIG. 14, a balloon catheter 170 has a distal inflatable balloon 172, inflation lumen 174 to deliver inflation fluid/media to the balloon, and an inner delivery lumen 176 used to deliver light activated adhesive and a delivery pusher 178 with a distal light 180 used to cure the light activated adhesive. Balloon catheter 170 would be tracked to the site of the LAA or vascular treatment site, and the distal end of the balloon catheter would be placed within the treatment site or at the neck of the treatment site. Balloon 172 is then expanded to seal the area adjacent to the neck of the treatment site to prevent any delivered embolic material from escaping. Alternatively, if the neck is large enough the balloon can physically placed within the neck of the LAA or vascular treatment site and expanded. Light-activated adhesive is delivered through delivery lumen 176 and delivery pusher 178 is subsequently delivered through the delivery lumen so that the distal end of delivery pusher 178 including light 180 are past the end of the delivery lumen. Delivery pusher 178 contains the appropriate battery and circuitry to light the light 180 (or alternatively, a proximal interface containing a battery can connect to the proximal end of delivery pusher 178). The light emitted from light 180 reacts with the light-activated adhesive already in the LAA/treatment site. Though there may be a lag between the time of the delivery of the light and the adhesive since the same delivery lumen 176 is used for both, the balloon prevents any of the adhesive from migrating in the interim. In one embodiment, delivery pusher 178 could utilize various mechanical, electrolytic, or thermal detachment systems well known in the art to detach the light 180 from pusher 178. In one embodiment, a dual-lumen balloon catheter could be used (similar to the dual-lumen concept of FIG. 4, except used with a balloon catheter) so that one lumen is used to deliver adhesive and another separate lumen is used for the delivery pusher. One advantage of a dual-lumen system is rapid curing since the delivery pusher 176 could be pre-delivered to the distal tip of its own lumen and the adhesive could be delivered through a separate lumen—however, the presence of balloon 172 mitigates many of these issues since the balloon prevents the adhesive from escaping between the time the adhesive is delivered and the time light 180 is delivered.

Figure 15:
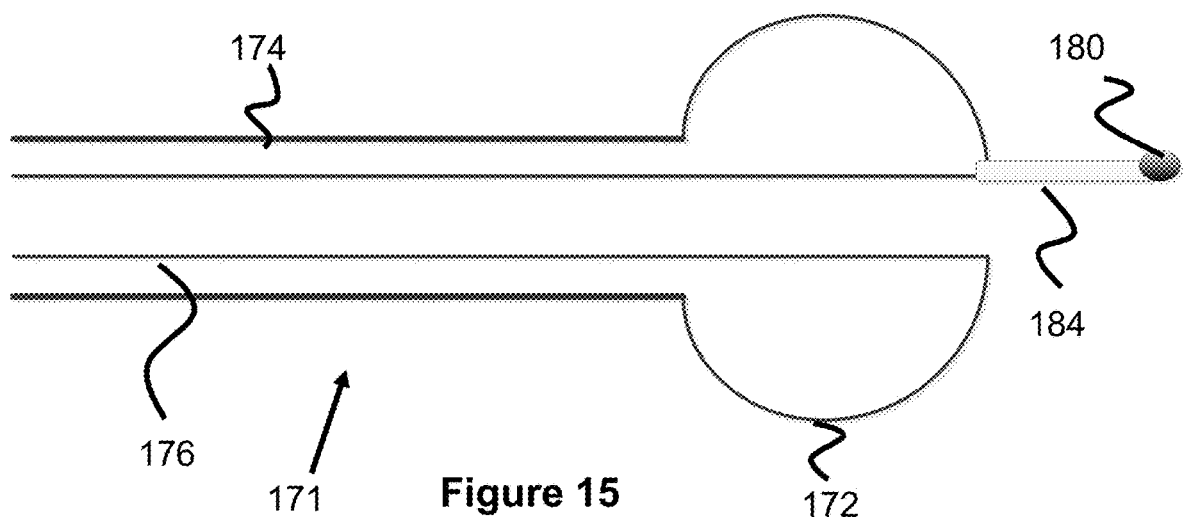
FIG. 15 illustrates a catheter with a light element, according to one embodiment.

In another embodiment, shown in FIG. 15, a balloon catheter 171 is used to deliver light-activated adhesive and the distal tip of the balloon catheter utilizes an extension 184 and a light 180 at the end of the extension. In this embodiment, there is no need to deliver a separate light source through lumen 176 since the light source is fixed to the distal tip of the balloon catheter. The balloon catheter would contain the appropriate circuitry to power the light and a proximal battery or interface could be used to power the light 180. In one example, a fiber optic or optical fiber member can be used as a structural reinforcement layer of the balloon catheter and span the length of the catheter, where this fiber optic/optical fiber member is used as the light 180 at the distal end of the balloon catheter. In one embodiment, extension 184 could utilize various detachment means (thermal, electrolytic, mechanical) to detach the light 180.

Additional variations of the balloon catheter concepts of FIGS. 14-15 are also possible. For instance, a mesh structure or a metallic frame or prop can be placed proximally adjacent to the balloon to help keep the balloon from contracting during adhesive delivery.

Figure 16:
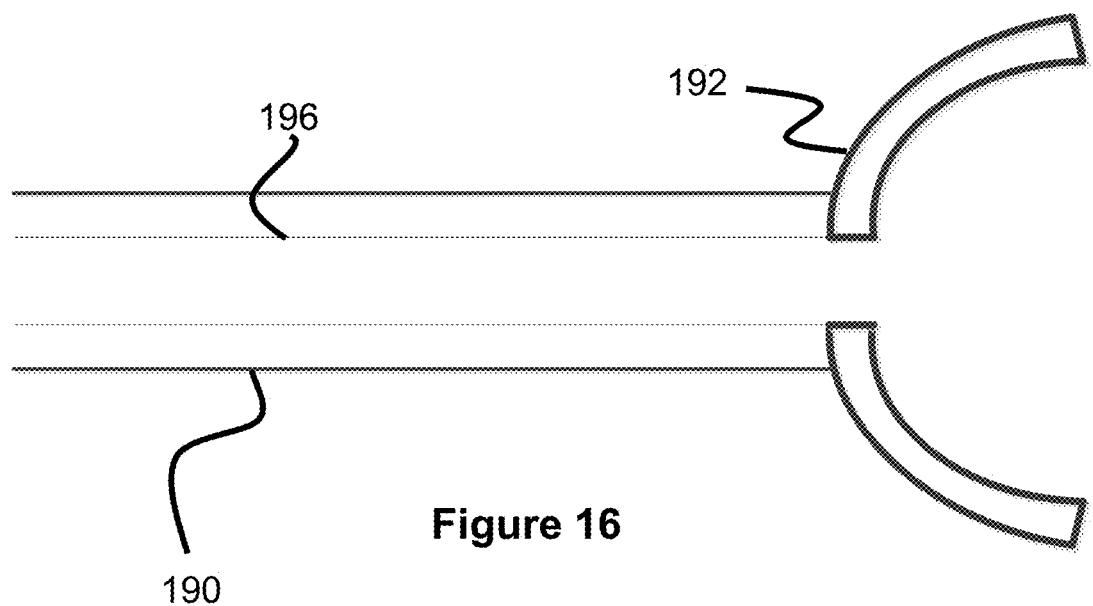
FIG. 16 illustrates a catheter with a blocking element, according to one embodiment.
Figure 17:
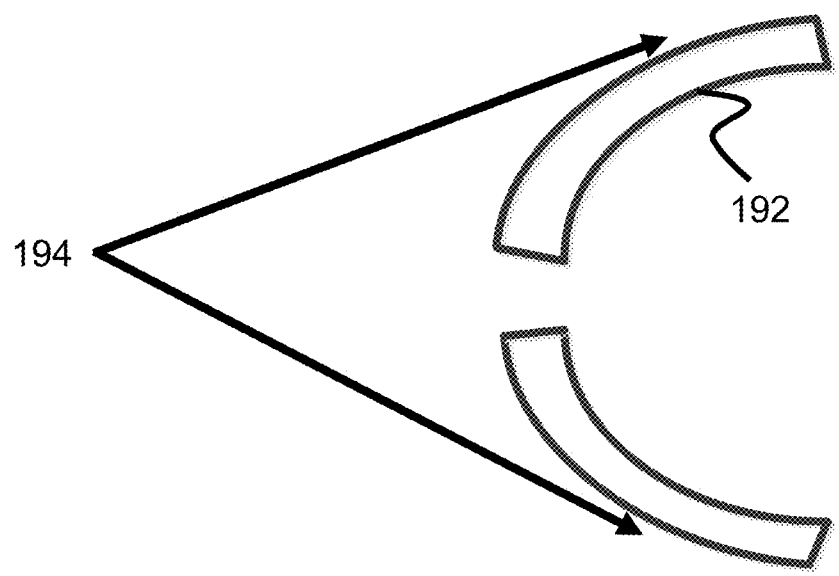
FIG. 17 illustrates a blocking element, according to one embodiment.

In another embodiment, shown in FIGS. 16-17, a retention structure 192 sits near the distal end of a catheter and acts to retain delivered light-activated adhesive within the treatment site. Retention structure 192 functions similar to sealing structure 120 of FIG. 5—with the exception being that the retention structure does not contain a light itself. Retention structure 192 can take on a number of configurations, including a mesh braided device or a solid metallic (e.g., nitinol) frame or polymeric structure. Catheter 190 is placed near the treatment site so that the retention structure 192 abuts the neck of the LAA/treatment site, or retention structure 192 can sit within the neck if sized appropriately. Adhesive is then delivered through catheter lumen 196 and retention structure 192 keeps the adhesive from escaping. A light source, similar to the light pusher structure 178 of FIG. 14 is then inserted within the lumen to react with the adhesive. Once the adhesive hardens, catheter 190 and attached retention structure 192 are withdrawn. In one embodiment, retention structure 192 has a thermal, electrolytic, or mechanical detachment system to detach the retention structure from the catheter to leave the retention structure in place afterwards.

In one embodiment, retention structure 192 can include adhesive at location 194 of FIG. 17. The adhesive would be pre-placed on the exterior of retention structure 192 at location 194 and partially or fully exposed to light in order to adopt a gel like or solidified consistency to prevent migration of the adhesive. If the adhesive is in a semi-solidified gel-like state, the exposure to light after delivery would solidify the adhesive—if the adhesive is already solidified prior to delivery of the retention structure 192 then the adhesive will be solidified when the retention structure is placed within the vasculature. In any event, the presence of the adhesive on the exterior of the retention structure 192 would seal any gaps between the retention structure and the LAA, ensuring that any subsequently delivered adhesive had no escape path past retention structure 192 prior to the time when the adhesive is exposed to light and cures or solidifies.

Please note light-curable adhesives, and systems used with light-curable adhesives were discussed. The chemistry of the adhesive itself will determine which frequency range of light will cure or harden the adhesive. In some embodiments, UV-frequency light is used to cure the adhesives and therefore the lights used to cure a UV-light curable adhesive are in the UV frequency range. According to Planck's equation ($E=h\nu$), Energy (E) is directly proportional to light frequency (v), such that a higher frequency corresponds to higher energy. Ultraviolet frequency light sits on the higher end of the frequency scale, which could lead to issues such as heat transmission during delivery. The specification discussed how shielding could be used to limit light or energy transmission away from the optical fiber or energy carrying medium. Similarly, light in a lower than UV-frequency range (e.g. "blue" or other color light in the red-orange-yellow-blue-indigo-violet-ultraviolet) range could be used to control possible heat transmission issues.

Figure 18:
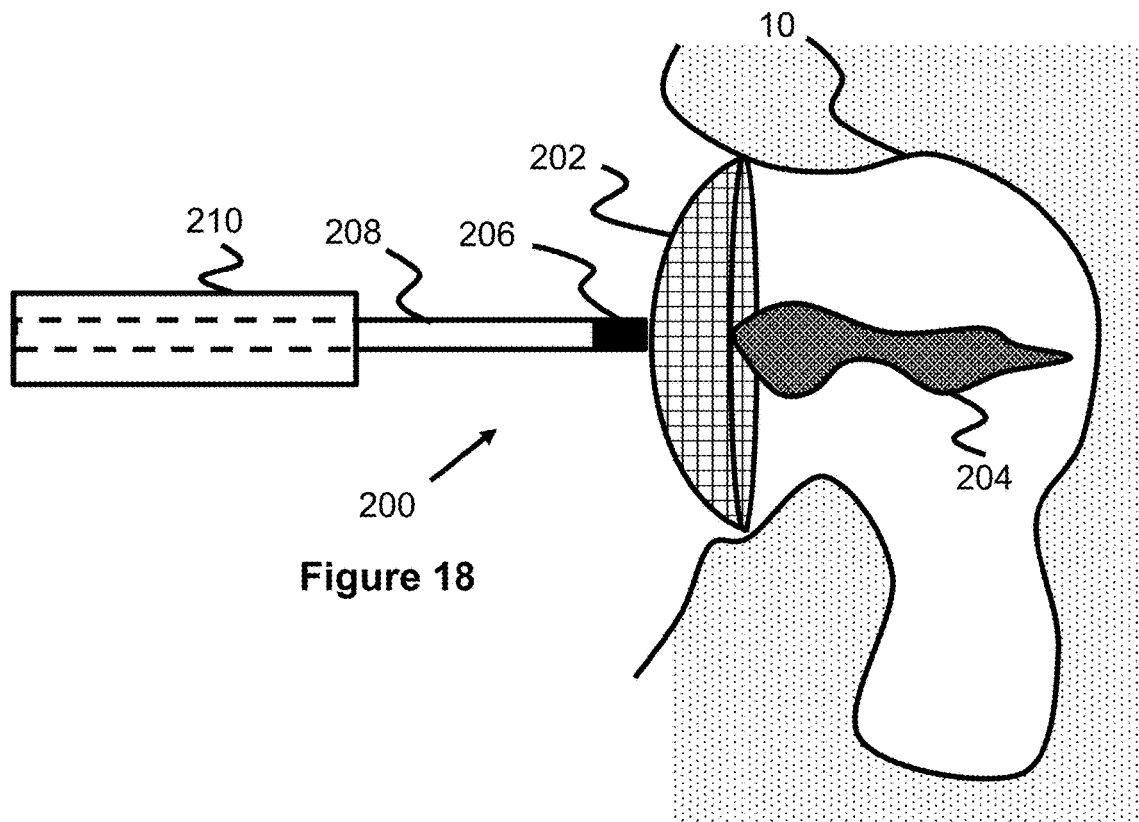
FIG. 18 illustrates a catheter with a retention structure and a balloon, according to one embodiment.
Figure 19:
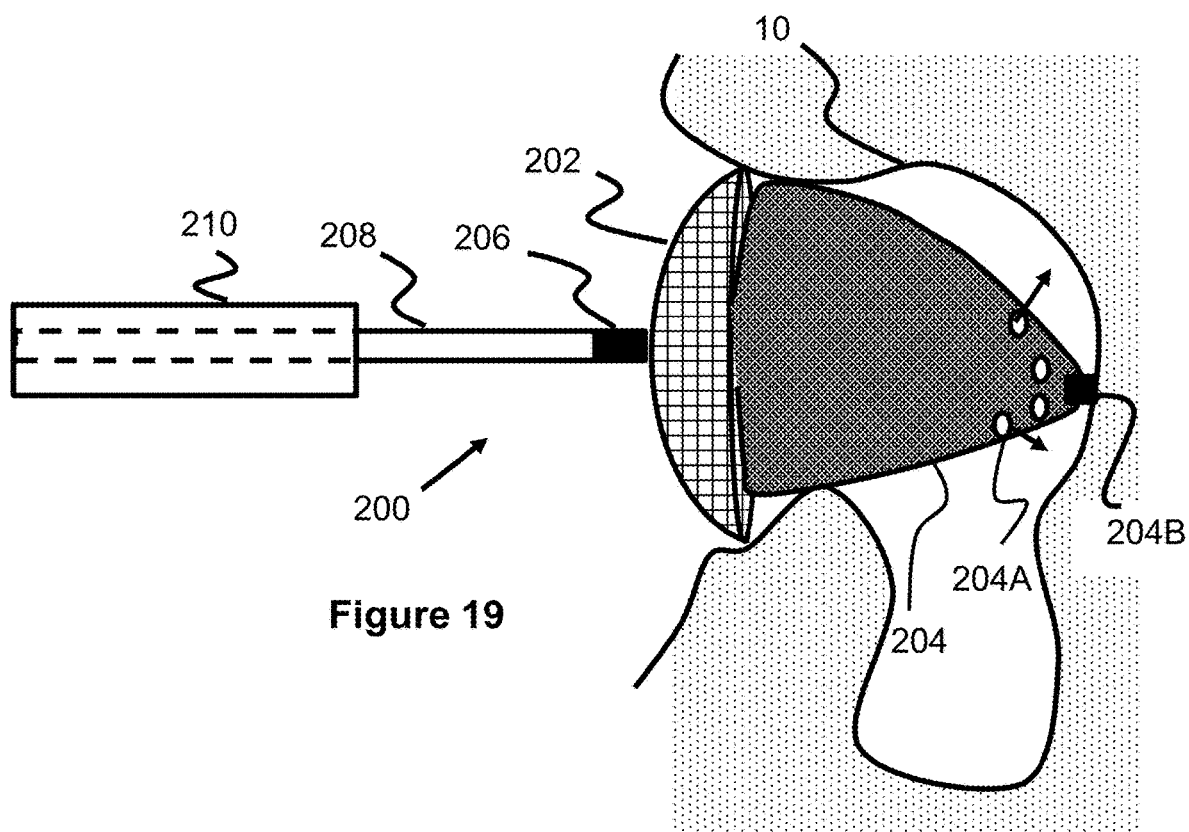
FIG. 19 illustrates a catheter with a retention structure and a balloon, according to one embodiment.
Figure 20:
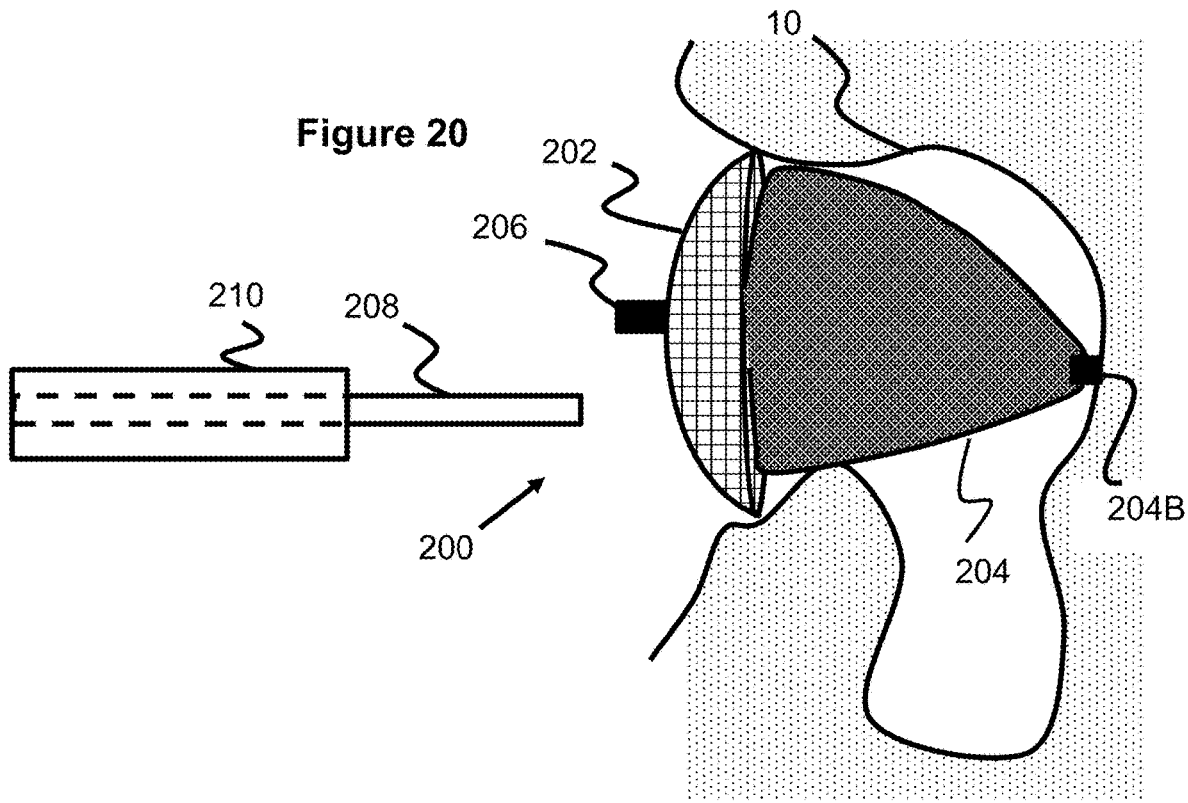
FIG. 20 illustrates a catheter with a retention structure and a balloon, according to one embodiment.

Other embodiments presented herein utilize a conformable structure, such as a balloon, to conform to part or all of the geometry of the target occlusive area (e.g. LAA). Adhesive is used along with the conformable structure to affix the conformable structure within the target occlusive area, thereby occluding the target area. FIGS. 18-20 illustrate another embodiment of an occlusion device 200 utilizing this concept where said occlusion device 200 can be particularly effective in occluding the left atrial appendage (LAA) 10 of a patient. Unlike the prior described embodiments, the device 200 includes both a retention structure 202 and an occlusion balloon 204 that can be used to deliver tissue adhesive into the LAA 10. Specifically, the retention structure 202 can be first expanded to block off the opening of the LAA 10, and then the balloon 204 can be expanded to deliver the tissue adhesives. These upcoming embodiments are primarily described with regard to traditional, non-light activated tissue adhesives. However, light-activated adhesives could also be used where the delivery system would include a curing light, similar to the delivery systems described above. Though these embodiments will be primarily described for use in treating LAA's and have particular utility in this function, these embodiments can be used to treat a variety of other vascular conditions including aneurysms, atrial septal defect, fistulas, etc. and have general utility in occluding space within the vasculature.

The device is primarily comprised of the pusher or catheter body portion 208 and the occlusion portion (e.g., the retention structure 202 and balloon 204) that selectively detaches from the catheter body portion 208, as seen in FIG. 20. Turning first to the occlusion portion, the retention structure 202 is, in one embodiment, composed of a mesh of braided wires that are heat-set to expand, when unconstrained, into a predefined radial shape. For example, FIGS. 18-20 illustrate a retention structure 202 with a dish-shaped, concave structure opening in a distal direction. In another example a device can have a cylindrical, cup-shaped retention structure. The retention structure may also take the expanded form of a relatively flat disc, an ovoid shape, a spherical shape, or other variations.

The occlusion balloon 204 is connected distally of the retention structure 202 and can be composed of a compliant material to allow unconstrained expansion as volume and pressure increase. For example, a highly elastic, low durometer urethane can be used. In another example, silicone, PeBax, or a combination of both can be used.

Figure 23:
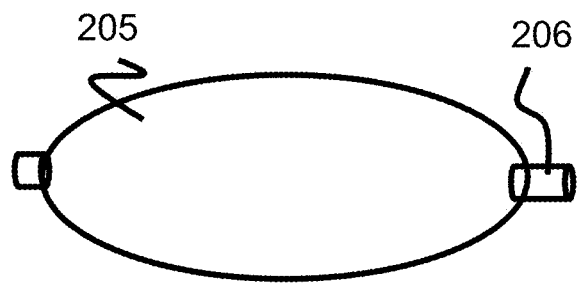
FIG. 23 illustrates an occlusion balloon, according to one embodiment.
Figure 24:
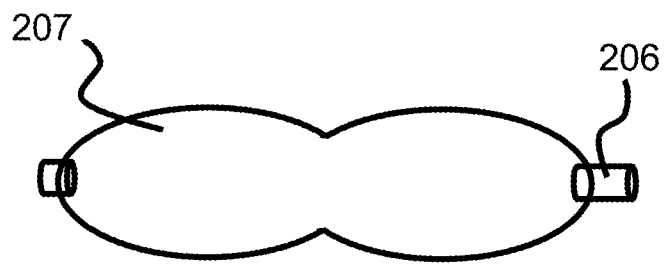
FIG. 24 illustrates an occlusion balloon, according to one embodiment.

In the embodiment of FIGS. 18-20 and 22, the balloon 204 has a generally conical shape, terminating with a distal radiopaque marker 204B and a proximal connection member 206. While the balloon 24 will initially expand to the generally conical shape, it may lose this shape and expand to a more rounded shape, depending on the volume of material injected into it. In one example, the balloon 204 expands to up to about 18-20 mm diameter (e.g. at its widest bottom portion) and about 18-35 mm in length (e.g. from the bottom portion that sits near the neck of the LAA to the top portion that sits near the dome/top of the LAA). Alternately, the balloon can have a generally rounded or oval shape (balloon 205, FIG. 23), two adjacent rounded shapes (balloon 207, FIG. 24), or any other variation of shapes. These measurements are only proffered by way of example and can be modified depending on the sizing characteristics of the LAA/vascular condition.

Figure 22:
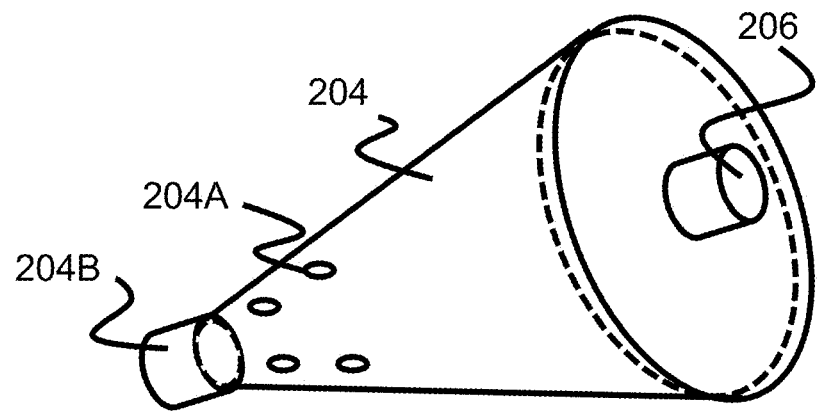
FIG. 22 illustrates an occlusion balloon, according to one embodiment.

In one embodiment, the balloon 204 includes a plurality of apertures 204A positioned near the balloon's distal end, as best seen in FIG. 22. Once inside the LAA 10, the balloon 204 is inflated or injected with tissue adhesive—in a process that will be explained in more detail later. The apertures 204A are sized to open as the balloon 204 expands and to allow the adhesive to leak into the LAA 10 slowly enough to allow the balloon 204 to fully inflate. Additionally, the distal location of the apertures 204A allows the proximal, enlarged portion of the balloon 204 to engage and seal the LAA 10 before any of the tissue adhesive can leak out into the heart.

In another embodiment, rather than being injected or inflated with tissue adhesive, the outer surface of the balloon 204 is instead covered with tissue adhesive. The balloon 204 is injected with saline, contrast agent, or hydrogel—in a process that will be explained in more detail later. Once the balloon 204 expands, the outer adhesive coating adheres to the tissue of the LAA 10, sealing the cavity off from the heart. Alternative embodiments can utilize a balloon with channels or pores linking the inner part of the balloon to the outer part of the balloon. The inner balloon surface, or the channels connecting the inner balloon surface and outer balloon surface can be coated with tissue adhesive. As the balloon is injected or inflated (e.g., with saline, contrast agent, or hydrogel), the tissue adhesive migrates or diffuses to the outer surface of the balloon, thereby adhering to the tissue of the LAA as the balloon expands to contact the interior surface of the LAA.

The tissue adhesive used can include cyanoacrylate or UV-activated glue. In one specific example, the tissue adhesive is n-Butyl Cyanoacrylate (nBCA) and Lipiodol (iodized poppy oil) in about a 9:1 ratio, respectively, and after use, Dextrose can be used to clear out the catheter 208.

In one embodiment, the occlusion portion can be created by laser welding a proximal radiopaque marker tube and a distal radiopaque marker tube on a proximal and distal side, respectively, of the mesh retention structure 202, creating a passage therethrough. The balloon 204 is then bonded onto the distal radiopaque marker tube to allow communication of the passage within the balloon 204. The proximal radiopaque marker tube is connected to the proximal connection member 206, which also contains a passage therethrough and is selectively disconnectable from the distal end of the catheter body 208.

The catheter/conduit 208 is a generally elongated tubular structure having at least one passage within it that is connected to the previously described passage through the occlusion portion. This passage allows for delivery of the tissue adhesive (or saline, contrast, hydrogel, etc.) from a proximal port to the interior of the balloon 204. Additionally, the catheter 208 may have additional passages and features (e.g., UV lamp if a light-activated tissue adhesive is used) as other catheters described in this specification.

Figure 21:
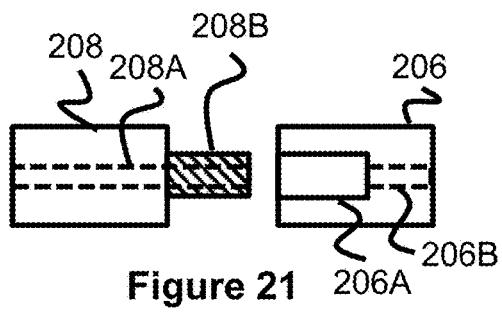
FIG. 21 illustrates a detachable joint, according to one embodiment.

The distal end of the catheter 208 is selectively connectable/disconnectable to the proximal end of the proximal connection member 206. In one embodiment, the two components are engaged with each other via mating threads, allowing the catheter 208 to be rotated on its axis until the threads disengage. For example, FIG. 21 illustrates the catheter body 208 having a reduced-diameter and distally extending male threaded portion 208B. This threaded portion 208B has a thread and diameter sized to engage the recessed, female portion 206A of the member 206. Once threaded together, the catheter's passage 208A connects to passage 206B of the member 206, which ultimately connects on to the interior of the balloon 204.

In alternate embodiments, different detachment mechanisms can be used. Different detachment mechanisms can be found in U.S. Pat. Nos. 8,182,506; 9,561,125; 9,867,622; and 9,877,729; each of which is incorporated herein in their entirety by reference. It should be understood that while some of these embodiments incorporated by reference do not include a passage between their pusher/catheter and implant, such a passage could be included to accommodate the use of balloon 204.

The detachment mechanism illustrated in FIG. 21 may include a simple, continuous open passage throughout, such that when detachment occurs, the passage 206B is still open to the environment. If the tissue adhesive has hardened/cured, then little or none of it should escape from the passage 206B into the heart. However, it may also be desirable to include a valve, such as a check valve or one-way valve, within the proximal connection member 206 (or elsewhere in the occlusion portion) to prevent backflow.

Figure 26:
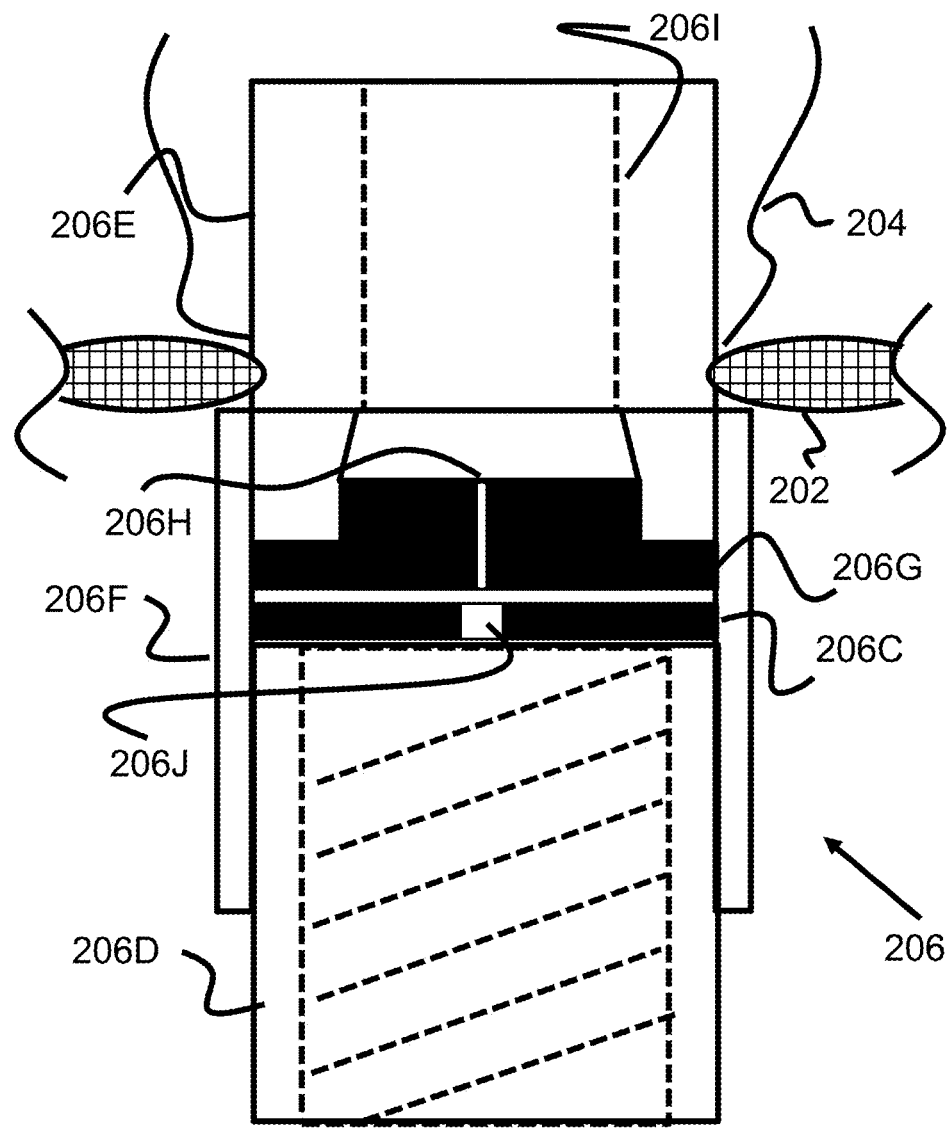
FIG. 26 illustrates a detachable joint with a valve, according to one embodiment.

FIG. 26 illustrates one example of a proximal connection member 206 with a valve that remains open when connected to the catheter body 208 but closes when detachment from the catheter body 208 occurs. An outer housing 206F is connected to a distal retainer portion 206E on which the retaining portion 202 and balloon 204 are affixed on, and to a threaded female insert portion 206D. A valve member 206G with a proximal gasket 206C having a center aperture 206J is located between portion 206E and 206D. When the male threaded portion 208B (shown in FIG. 21) of the catheter 208 is threaded into the threaded female insert portion 206D, its distal end presses against the gasket 206C, which in turn presses against the valve member 206G, causing a central slit 206H or passage in the member 206G to open into passage 206I in portion 206E, which ultimately opens to the interior of the balloon 204. In this respect, a passage is created between the male threaded portion 208B, through aperture 206J, through slit 206H, into passage 206I, and finally into the balloon 204. Once the male threaded portion 208B is removed from the female threaded interior of the threaded female insert portion 206D, pressure is removed from the valve member 206G, causing the slit 206H of the valve member 206G to close and prevent backflow from the proximal connection member 206 and into the heart.

Alternately, the valve member 206G can be a one-way valve member. For example, the valve member 206G can be a one-way duck-billed valve member or an umbrella valve member.

Both the catheter body 208 and the occlusion portion (which includes retention structure 202 and balloon 204) can be advanced through a larger delivery or guide sheath/catheter 210 or can be preloaded within an outer sheath/catheter that can be retracted to release the occlusion portion once located within the LAA 10.

The LAA treatment procedure involves making a septal puncture in the heart under ultrasound/echocardiography, and a larger delivery conduit housing the occlusive device/delivery catheter is advanced through the puncture. The LAA location and shape is checked under fluoroscopy. A larger delivery sheath or delivery catheter 210 is pushed into the LAA, and the smaller inner catheter 208 is tracked to a distal portion of the outer sheath. Catheter 210 is withdrawn so as to expose the shield retention structure and catheter 208 is also retracted, such that the retention element 202 radially expands to circumferentially contact the opening of the LAA 10, as seen in FIG. 18. Proximal displacement of the catheter 208 as it sits within the LAA during this delivery step will ensure that the shield structure is moved proximally to the location of the LAA neck as the shield expands, thereby ensuring the shield is properly seated at the neck or opening of the LAA. The larger delivery sheath 210 can optionally be used to provide a retention force against the proximal end of retention element 202 for proper seating. Alternative delivery methods can utilize pushing catheter 208 distally to expose the shield structure, or retracting outer delivery sheath/catheter 210 when said sheath 210 is positioned near the neck of the LAA, however care should be taken to ensure the shield structure is seated properly at the neck of the LAA.

Adhesive (or alternatively—saline, contrast agent, or hydrogel) is then injected through the proximal end of catheter element 208 (e.g., through a syringe mated to the catheter hub), through its internal passage 208A, through proximal connection member 206, and into balloon 204 to fill the balloon. If adhesive is injected and apertures 204A are present on the distal end of the balloon 104, the adhesive leaks out into the far end of the LAA 10 as the proximal portion of the balloon 204 radially expands to seal off the opening of the LAA 10, as seen in FIG. 19. Alternately, if no apertures are present, the balloon 204 expands until a layer of adhesive on its outer surface contacts and adheres to the tissue of the LAA 10.

Fluoroscopy can be used to ensure proper curing and stability of the injected fluid, and proper occlusive positioning of the balloon. The delivery sheath 210 is retracted if it is still pinned against the retention structure, and the smaller catheter 208 (which is also used as the adhesive conduit) is disengaged from the occlusive device (either through mechanical rotation as outlined earlier, or through the alternative detachment methods presented). The physician can perform a final echocardiogram and angiogram to verify the proper positioning of the occlusive device before inner catheter 208 and outer catheter 210 are withdrawn and procedure is terminated.

In an alternative delivery procedure, no outer sheath/catheter 210 is used and instead only the catheter 208 housing the actual occlusive device is used. Such an arrangement is feasible, for instance, in situations where the blood vessels may be smaller (e.g., for juvenile patients).

Alternative occlusion embodiments can utilize an occlusive balloon, but no holes. Instead, the balloon is made of a highly conformable material which conforms to the geometry of the LAA. The balloon is filled with an inflation fluid (e.g., saline, contrast agent, hydrogel, or adhesive). The balloon is optionally further pre-coated with an adhesive substance such that the balloon sticks to the occlusive space as the balloon expands. Alternatively, the balloon is not pre-coated with adhesive and the filling force provided by the balloon filling agents is sufficient to cause the balloon to stick and conform to the target occlusive space. The check valves described above can also be used to ensure the balloon filling fluids do not leak out from the balloon through the delivery catheter/conduit. After the balloon is filled, the delivery catheter connected to the mesh structure and balloon is detached and withdrawn. In alternative embodiments, the balloon contains channels and an adhesive material is pre-contained within the channels or within the interior balloon surface in fluid communication with the channels. As the balloon expands, the adhesive is pushed out from the balloon to the balloon outer surface and adheres to the vessel wall.

Figure 25:
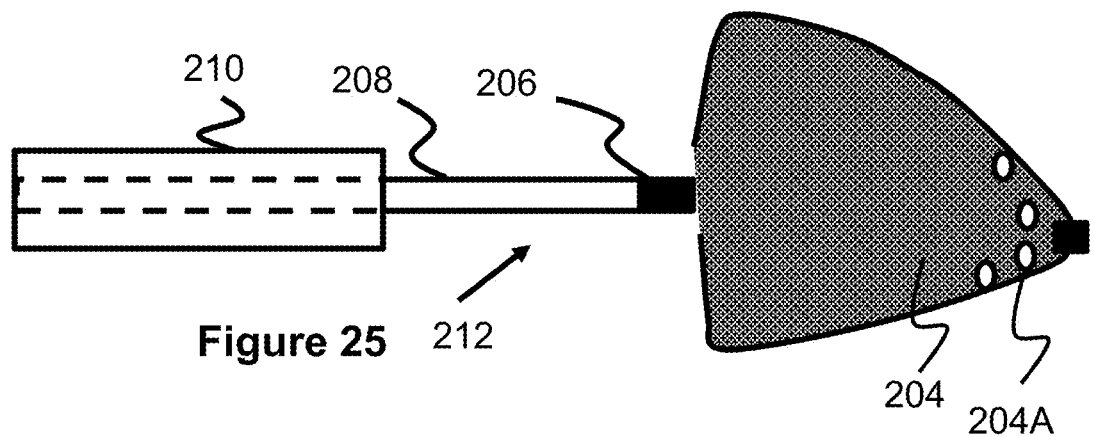
FIG. 25 illustrates a catheter with a retention structure and a balloon, according to one embodiment.

Some embodiments may forego a retention structure entirely. For instance, in circumstances where adhesive is not used to fill the balloon (e.g., in embodiments where the balloon is pre-coated with an adhesive on the outer surface, or those embodiments where the balloon is filled with contrast agent or saline), a retention structure may not even be necessary since there would be no issues from adhesive potentially leaking out from the LAA/balloon. FIG. 25 illustrates another embodiment of a device 212 in line with these principles, that is similar to the previously described device 200, but lacks retention structure 202. In other words, the device 212 only includes a balloon 204 that is delivered within a LAA 10 and expanded to cause occlusion. As with the previously described balloon 204, it may include distal apertures 204A that allow tissue adhesive delivered into the balloon 204 to escape into the LAA 10. Alternately, the balloon may lack the apertures 204A, be filled with a non-adhesive material (e.g., saline, contrast), and have an adhesive coating on its outer surface that allows it to adhere to the interior of the LAA 10. As with prior embodiments, the balloon 204 can be detached from the catheter 208 at the proximal connection member 206.

Figure 27:
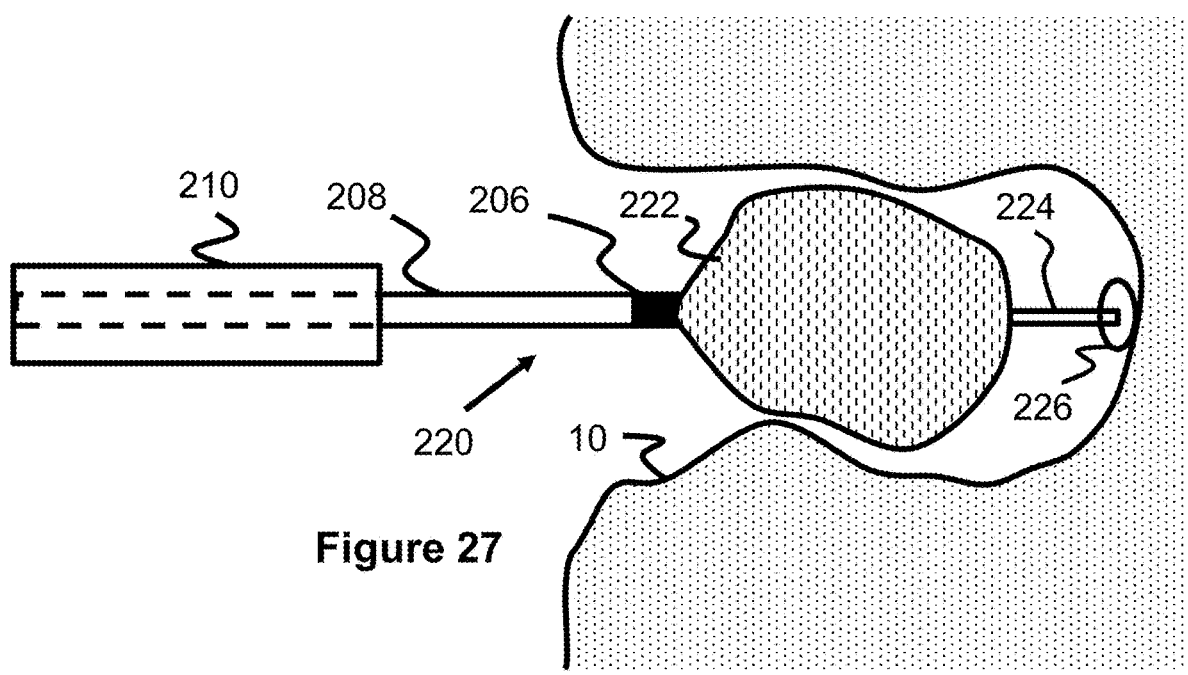
FIG. 27 illustrates a catheter with a foam plug, according to one embodiment.
Figure 28:
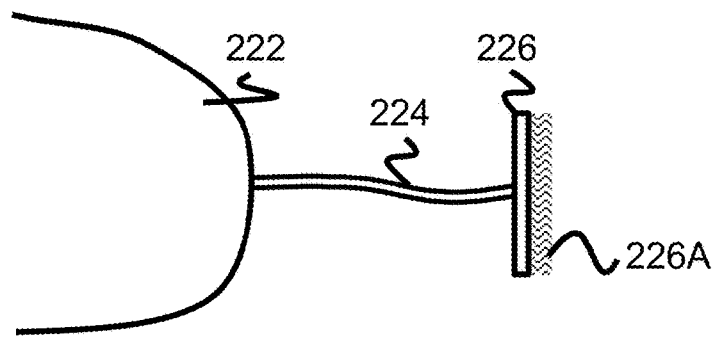
FIG. 28 illustrates a catheter with a foam plug, according to one embodiment.

Some embodiments may forego the use of a balloon and instead utilize alternative filling structures. FIGS. 27 and 28 illustrate another embodiment of an occlusion device 220 that is particularly suited for treatment of a LAA, among other uses, utilizing this principle. Specifically, the occlusion device 220 includes a plug of open cell foam 222 fixed to the proximal connection member 206 of the catheter 208. As best seen in FIG. 28, the distal end of the plug 222 includes a rigid or semi-rigid tether 224 that is connected to a distal anchor member 226. The distal anchor member 226 provides a distally facing surface (e.g., a circular plate) that adheres to an interior surface of an LAA 10 to thereby anchor the plug 222 in place. The catheter 208 can be detached from the proximal connection member 206 (e.g., via one of the previously described detachment mechanisms), leaving the plug 222 within the LAA 10. Over time, tissue will grow into the plug 222, fully occluding the LAA 10.

In one embodiment, the anchor member 226 has a distal surface having tissue adhesive 226A on it. In another embodiment, the distal surface has barbs, spikes, or similar penetrating anchoring mechanisms.

Figure 29:
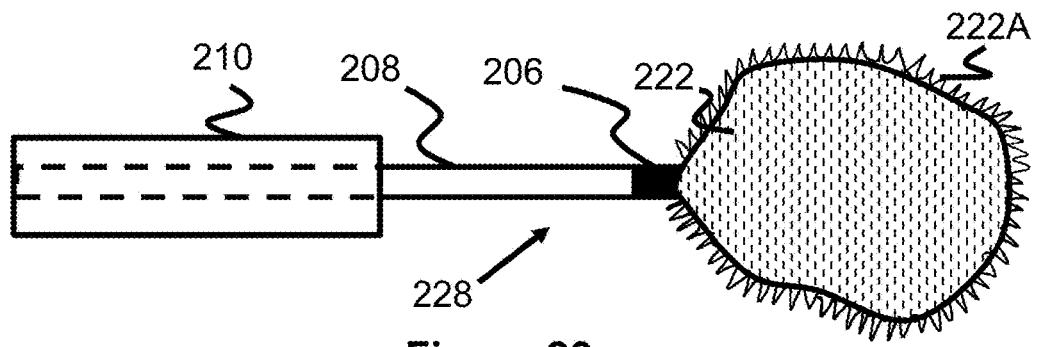
FIG. 29 illustrates a catheter with a foam plug, according to one embodiment.

In one embodiment, the plug 222 of the device 220 can be pre-coated in a tissue adhesive or can be injected with a tissue adhesive (e.g., an adhesive delivering tube can be positioned to open at the proximal end of the plug 222, allowing the adhesive to "weep" out of the plug 222. The device 228 of FIG. 29 illustrates such a plug 222 with an outer adhesive layer 22A, either pre-coated or injected into the plug 222. Additionally, in such an adhesive-coated embodiment 228, the tether 224 and anchor member 226 can be omitted.

In any of the embodiments with the open cell foam plug 222, the foam can be composed of various materials such as starch, chitosan, biodegradable urethanes, biocompatible urethane, and materials that can absorb and capture blood to enhance swelling.

Figure 30:
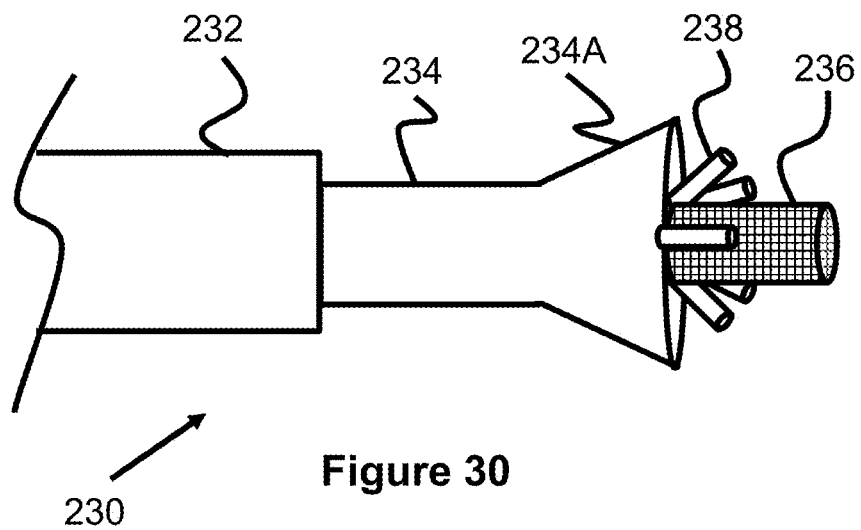
FIG. 30 illustrates a suction and adhesive-delivering catheter, according to one embodiment.
Figure 31:
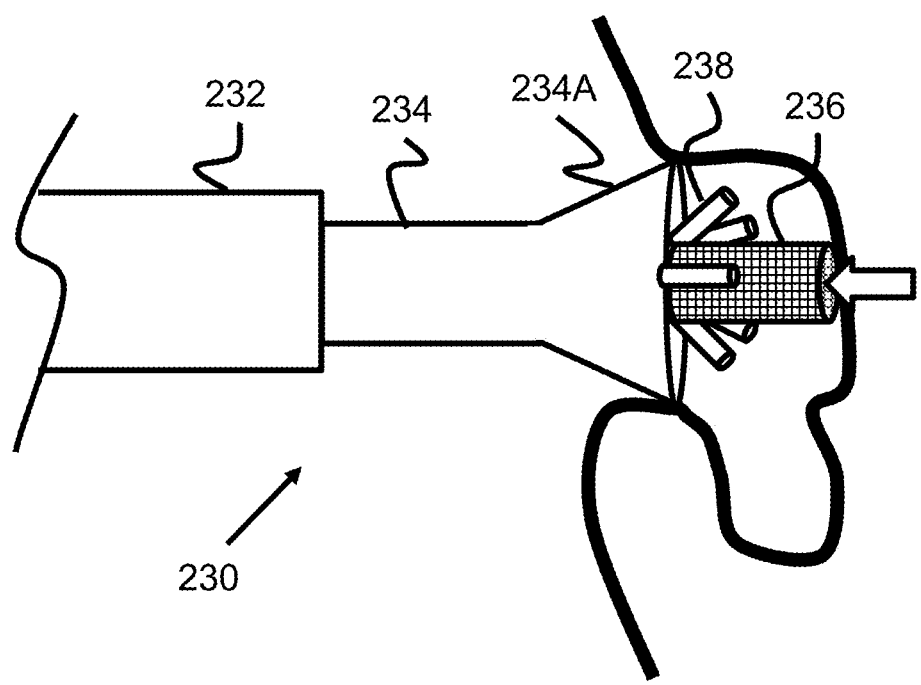
FIG. 31 illustrates a suction and adhesive-delivering catheter, according to one embodiment.
Figure 32:
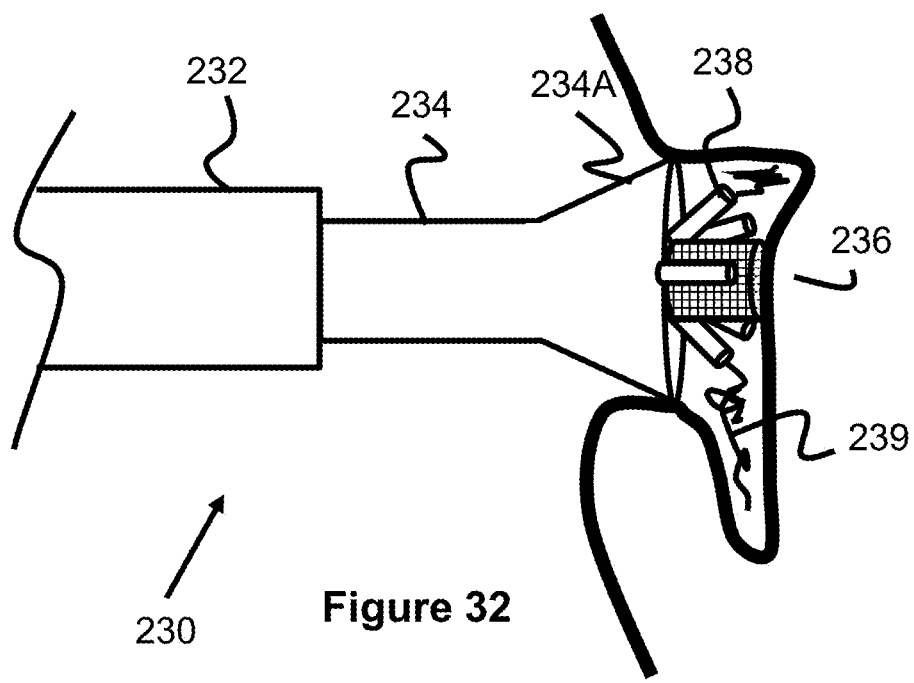
FIG. 32 illustrates a suction and adhesive-delivering catheter, according to one embodiment.

In some embodiments, suction can be used to collapse the vascular structure (e.g., LAA) to augment or replace occlusion. FIGS. 30-32 illustrate another embodiment of a device 230 for occluding a portion of a vessel, such as a LAA 10, utilizing this principle. The device 230 includes an outer introducer sheath 232 having a distal end that is initially placed near the opening of the LAA 10. A shield sheath 234, having an enlarged, conical distal end 234A is advanced distally until the end 234A contacts and blocks off the opening of the LAA 10, as seen in FIG. 31. Once blocked off, a suction catheter 236 is distally advanced out of the shield catheter 234 until its distal end is in contacts with an inner surface of the LAA 10. Suction is then applied through the suction catheter 236, causing the distal end of the catheter 236 to be fixed or anchored within the LAA 10. Next, the suction catheter 236 is proximally withdrawn towards the shield catheter 234 to reduce the size of the LAA 10, as seen in FIG. 32.

Once the size of the LAA 10 has been reduced, tissue adhesive 239 is injected to maintain the new size of the LAA 10. In that regard, the device 230 further includes a plurality of adhesive delivery tubes 238 that terminate at locations around the suction catheter 236 and are connected to an injectable supply of tissue adhesive 239 at the proximal end of the device. Once the adhesive 239 has been ejected from the tubes 238, has filled the LAA 10, and hardened, the device 230 can be removed.

As previously discussed, fluoroscopy is typically used to visualize occlusion devices for a LAA treatment procedure. In that respect, liquid contrast agents are often injected into the patient (e.g., into the catheter and balloon or external of the closure device). However, contrast agents are not always well-tolerated by patients with renal disease.

Figure 33:
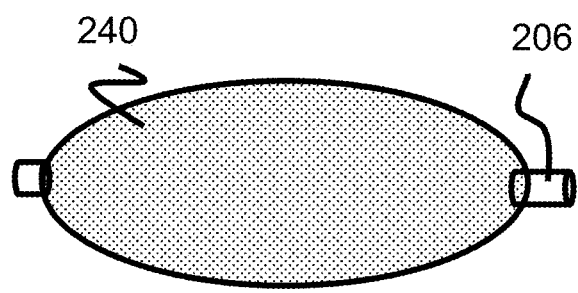
FIG. 33 illustrates an occlusion balloon, according to one embodiment.
Figure 34:
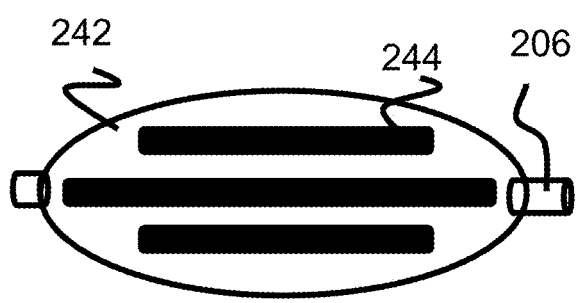
FIG. 34 illustrates an occlusion balloon, according to one embodiment.
Figure 35:
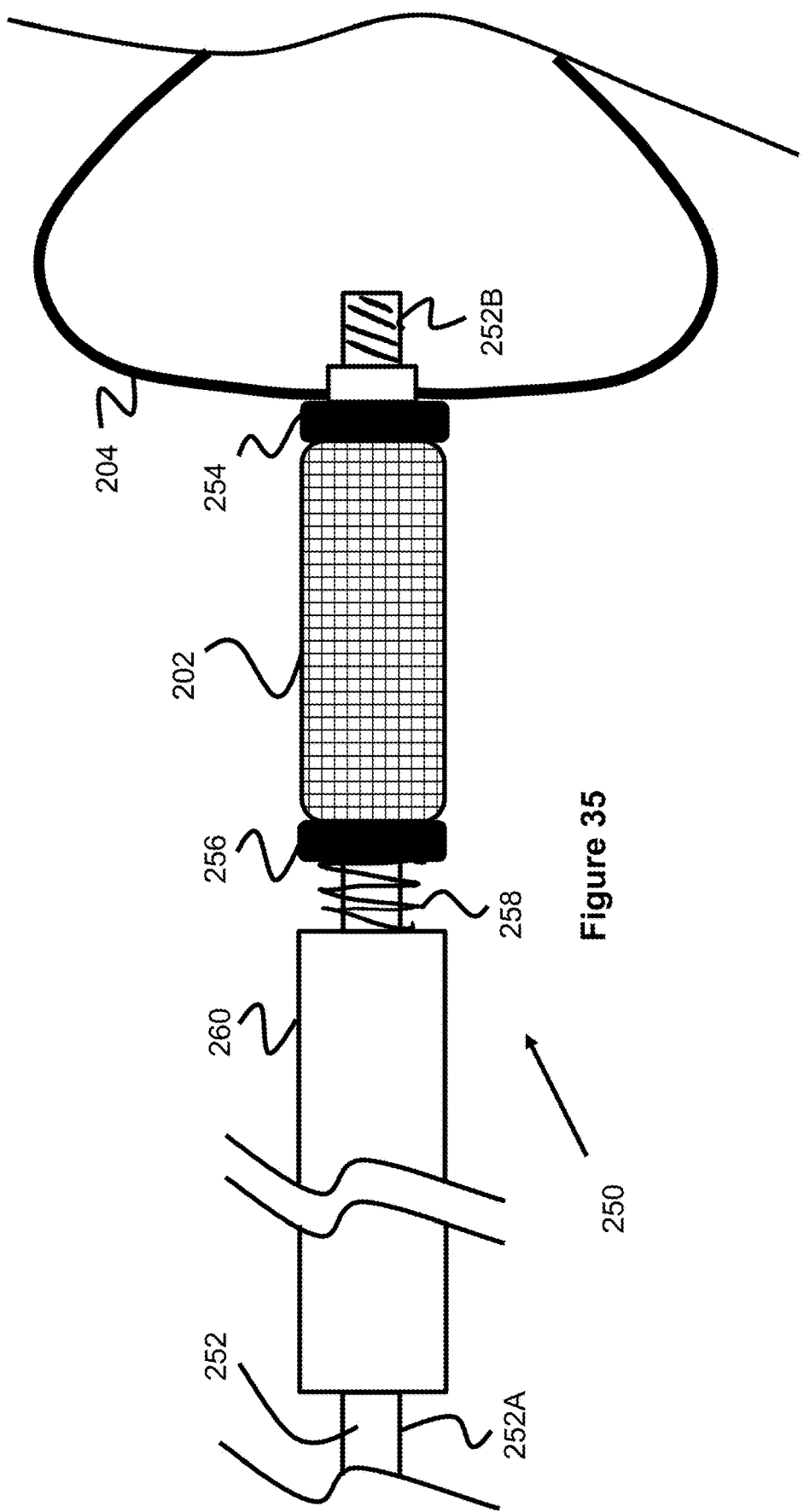
FIG. 35 illustrates a catheter with an occlusion device, according to one embodiment.
Figure 36:
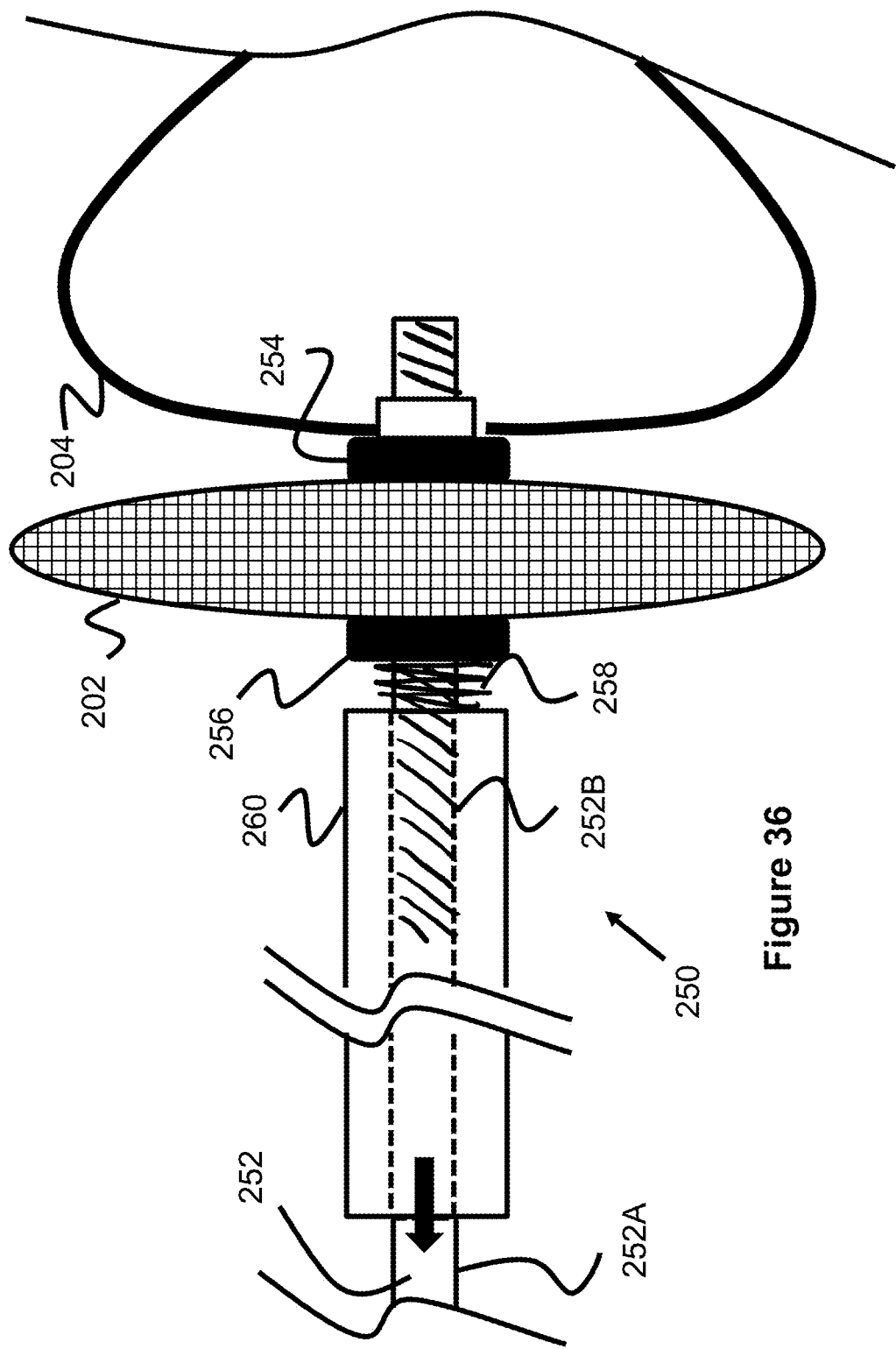
FIG. 36 illustrates a catheter with an occlusion device, according to one embodiment.

FIG. 33 illustrates a balloon 240 that can be used with any of the prior-described embodiments and which is visible under fluoroscopy without the use of contrast agents or externally injected contrast agents. Specifically, the balloon is composed of a urethane resin with a small percentage of one or more of the following radiopaque materials: barium sulfate, tungsten, iodine, gold, bismuth trioxide, bismuth subcarbonate, or bismuth oxy chloride. As seen in FIG. 33, the entire balloon can be composed of this radiopaque material. Alternately, as seen in FIG. 34, the balloon 242 can be composed primarily of non-radiopaque material and can further have a plurality of radiopaque strips 244 composed of the above-mentioned materials that are printed or adhered onto the inner or outer surface of the balloon 242.

Several of the previous embodiments included a retention structure sitting at or near the neck of the vascular treatment site to aid in keeping the occlusive device within the target area. The following embodiments utilize a retention structure that has a first elongated, radially compressed shape and a second radially expanded shape, where the user can control the shape—advantages of this approach include the ability to treat a wide variety of differently sized LAA's and easier delivery through the outer delivery sheath since the retention structure does not automatically take on its fully expanded shape upon delivery. FIGS. 35-38 illustrate another embodiment of an occlusion device 250 that can be used for treatment of a LAA, among other uses, in line with this principle. The device 250 includes an inflatable balloon 204 and an expandable retention portion 202, similar to previously described embodiments. However, the device 250 further includes a mechanism for adjusting the diameter of the retention portion 202.

The adjustment mechanism includes an elongated inner core member 252 that is positioned in an outer sheath or tubular structure 260. The proximal portion 252A of the core member 252 extends out the proximal end of the catheter 208 and may optionally include a handle to allow the user to rotate it relative to the catheter 208. The distal portion of the member 252 includes a threaded portion 252B which, as described below, is removable from the proximal portion 252A at the end of a procedure so as to leave the occlusion portion in the LAA of the patient.

The retention portion 202 is fixed to a distal collet 254 that is positioned on the threaded portion 252B and fixed at a longitudinal position on the threaded portion 252B and can, along with the retention portion 202, either rotate freely or along with the threaded portion 252B. The proximal end of the retention portion 202 abuts proximal collet 256, which has a thread that is threaded on to the thread of the threaded portion 252B. If the core member 252 is rotated, all of the components on the distal threaded portion 252B (e.g., collets 254, 256, and retention structure 202) would also rotate and no changes would occur. However, the outer sheath 260 includes an engagement mechanism that can engage the proximal collet 256, allowing the user to prevent the threaded proximal collet 256 from rotating. In this state, rotating the inner core member 252 in a predetermined direction longitudinally moves the threaded proximal collet 256 in the distal direction. Hence, rotating the inner member 252 can move the proximal collet 256 from the position in FIG. 35 to the position in FIG. 36, causing the retention member 202 to radially increase in size. Depending on how far the proximal collet 256 is moved, the radial size of the retention member 202 can be determined by the user, depending on the size of the target LAA. Once expanded, a passage through the inner member 252 can be used to deliver adhesive or saline/contrast into the balloon 204 as described in other embodiments.

Figure 37:
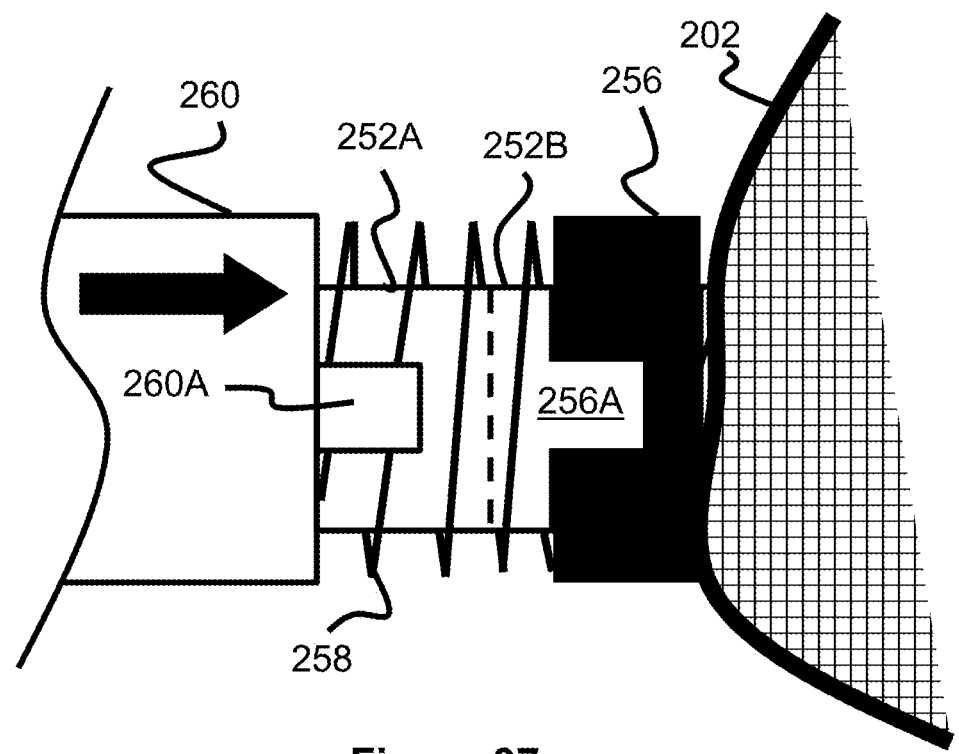
FIG. 37 illustrates a detachable joint for an occlusion device, according to one embodiment.
Figure 38:
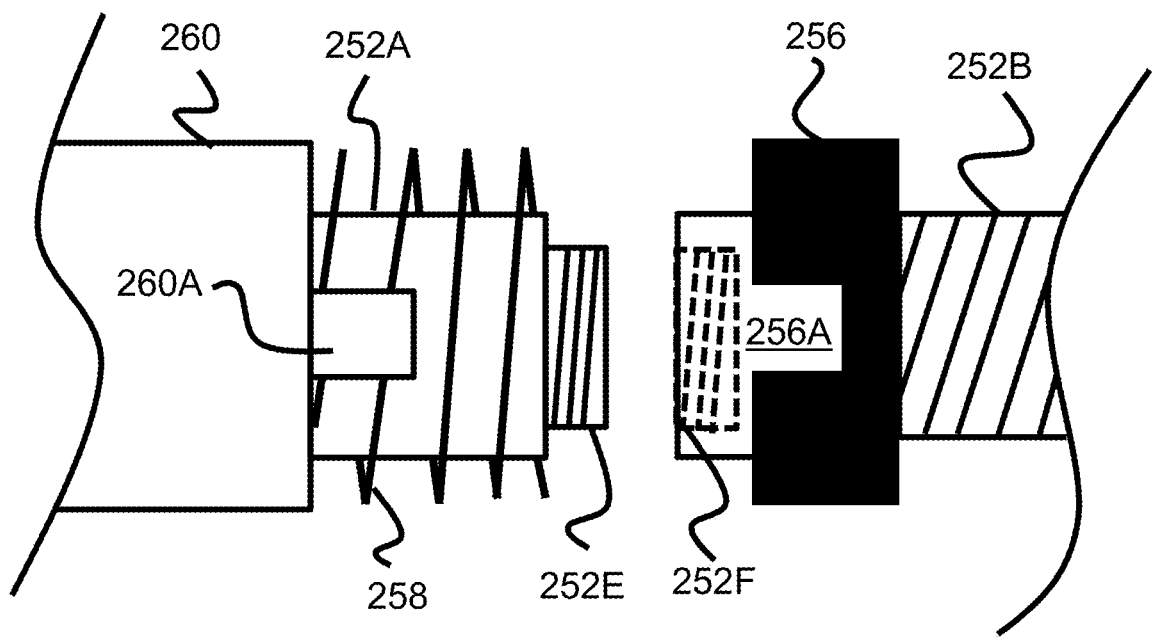
FIG. 38 illustrates a detachable joint for an occlusion device, according to one embodiment.

The engagement mechanism between the outer sheath 260 and the threaded proximal collet 256 can be best seen in FIGS. 37 and 38, including one or more tabs 260A (e.g., four positioned at 90 degrees from each other) extending distally from the distal edge of the outer sheath 260. The outer sheath 260 can be distally advanced relative to the inner member 252 (or vice versa), so that the tab 260A engages a mating recess or slot 256D in the proximal collet 256. This engagement causes the proximal collet 256 to rotate with the outer sheath 260, not the inner core member 252. A user can then rotate the core member 252 while holding the outer sheath 260 in place. Again, in a predetermined first direction, the proximal collet 256 will move proximally, causing the retention structure 202 to expand. To prevent accidental engagement of the mechanism, a spring 258 is disposed around the proximal portion 252A, fixed at its proximal end to outer sheath 260, and abuts the threaded proximal collet 256. This provides a biasing force to keep the tabs 260A out of engagement with slots 256A.

The above-described engagement mechanism can also be used to cause separation of the proximal portion 252A from the threaded distal portion 252B. As best seen in FIG. 38, the distal threaded portion 252B is screwed/threaded on to the proximal portion 252A via the female threaded portion 252F and the male threaded portion 252E, respectively. Preferably, the threads of portions 252E and 252F are such that they unscrew in a second predetermined direction, opposite of the first predetermined direction that moved the proximal collet 256 distally. Once separated, the proximal portion 252A and outer sheath 260 can be removed from the patient, leaving the distal threaded portion 252B and all of the components attached thereto.

Additional variations to the embodiments presented herein are possible. An anti-thrombogenic coating can be used either on the shield retention structure, balloon, or both. One such anti-thrombogenic coating that can be used is described in US Pub. No. 2018/0093019 which is hereby incorporated by reference in its entirety. Endothelial growth factor coatings can be used to facilitate tissue growth over the device, the coating can be used on the shield retention structure, balloon, or both. The balloon can have various shapes and surface characteristics to enhance friction and sticking force between the balloon and target treatment area—for instance, ribs and indentations can be used all along the balloon or in select regions of the balloon. The balloon, in some embodiments, can be biodegradable such that the balloon naturally biodegrades and disappears over time. Various filling materials can be used, as described above, to fill the balloon—for instance saline, contrast agent, hydrogel (degradable or non-degradable), oils, and/or adhesives. In other embodiments, other polymerizing materials (such as liquid embolic, which harden or precipitate in response to blood exposure) can be used. Some types of liquid embolics which can be used are disclosed in U.S. Pat. Nos. 9,351,993 and 9,078,950—both of which are hereby incorporated by reference in their entirety.

The principles and embodiments discussed within the specification have generally been discussed for use with light-curable adhesives and tissue adhesives which bind to the vascular tissue itself. These systems can also be used with light-curable liquid embolics where the liquid embolic solidifies based on exposure to light. As discussed earlier, the distinction between embolic and adhesive is that adhesives physically adhere to tissue.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusion device for treatment of a medical condition, comprising:
    an elongated conduit having at least one passage between its proximal end and distal end, the elongated conduit conveying an inflation fluid; and
    an inflatable balloon detachably connected to a distal portion of the conduit; the balloon being in communication with the at least one passage of the conduit to convey the inflation fluid to inflate the balloon;
    wherein a distal region of the inflatable balloon comprises a plurality of pores;
    wherein, in a non-inflated configuration, an adhesive is within an interior region of the inflatable balloon; and,
    wherein, in an inflated configuration, at least a portion of the adhesive is delivered through at least some of the plurality of pores.

2. The occlusion device of claim 1, wherein the distal region of the inflatable balloon comprises a porous membrane including the plurality of pores.

3. The occlusion device of claim 1, further comprising a retention structure positioned proximal of the inflatable balloon.

4. The occlusion device of claim 3, wherein the retention structure comprises a mesh braided device.

5. The occlusion device of claim 3, wherein the retention structure comprises a metallic frame.

6. The occlusion device of claim 3, wherein the retention structure comprises a polymeric structure.

7. The occlusion device of claim 3, further comprising a light source insertable within the at least one passage so as to react with the adhesive.

8. The occlusion device of claim 3, wherein the retention structure includes a detachment system for detaching the retention structure from the elongated conduit.

9. The occlusion device of claim 8, wherein the detachment system is comprised of a thermal detachment system.

10. The occlusion device of claim 8, wherein the detachment system is comprised of an electrolytic detachment system.

11. The occlusion device of claim 8, wherein the detachment system is comprised of a mechanical detachment system.

12. The occlusion device of claim 3, wherein the retention structure is positioned at or near the distal end of the elongated conduit.

13. The occlusion device of claim 1, further comprising one or more check valves to prevent backflow as the inflatable balloon is inflated.

14. The occlusion device of claim 13, wherein the one or more check valves are located in the conduit.

15. The occlusion device of claim 1, further comprising a threaded detachment assembly removably connecting the inflatable balloon to the conduit.

16. The occlusion device of claim 15, wherein the detachment assembly includes a threaded male portion engaged with a threaded female portion, such that rotation of the conduit detaches the conduit from the inflatable balloon.

17. An occlusion device, comprising:
    a delivery means for conveying an inflation fluid, the delivery means having at least one passage between its proximal end and distal end; and
    an inflation means in fluid communication with the at least one passage; and, wherein a distal region of the inflation means comprises a plurality of pores;

wherein, in a non-inflated configuration, an adhesive is within an interior region of the inflation means;

wherein, in an inflated configuration, at least a portion of the adhesive is delivered through at least some of the plurality of pores.

18. The occlusion device of claim 17, further comprising a retention means positioned proximal of the inflation means.

* * * * *